United States Patent
Coleman et al.

(10) Patent No.: US 10,799,242 B2
(45) Date of Patent: Oct. 13, 2020

(54) ADJUSTABLE HEART VALVE IMPLANT

(71) Applicants: James E. Coleman, Dublin (IE); Christy Cummins, Johnstown Naas (IE)

(72) Inventors: James E. Coleman, Dublin (IE); Christy Cummins, Johnstown Naas (IE)

(*) Notice: Subject to any disclaimer, the term of this patent is extended or adjusted under 35 U.S.C. 154(b) by 0 days.

(21) Appl. No.: 16/795,082

(22) Filed: Feb. 19, 2020

(65) Prior Publication Data
US 2020/0178977 A1    Jun. 11, 2020

Related U.S. Application Data

(63) Continuation of application No. 15/852,658, filed on Dec. 22, 2017, which is a continuation of application
(Continued)

(51) Int. Cl.
*A61B 17/12* (2006.01)
*A61F 2/24* (2006.01)
(Continued)

(52) U.S. Cl.
CPC .... *A61B 17/12031* (2013.01); *A61B 17/0057* (2013.01); *A61B 17/12109* (2013.01);
(Continued)

(58) Field of Classification Search
CPC .................................................. A61F 2/2436
See application file for complete search history.

(56) References Cited

U.S. PATENT DOCUMENTS

| 5,324,306 A | 6/1994 | Makower et al. |
| 6,260,552 B1 | 7/2001 | Mortier et al. |

(Continued)

FOREIGN PATENT DOCUMENTS

| CN | 1882293 A | 12/2006 |
| CN | 101184454 B | 10/2010 |

(Continued)

OTHER PUBLICATIONS

International Search Report and Written Opinion for Application No. PCT/EP2014/075162, dated Feb. 13, 2015 (13 pages).
(Continued)

*Primary Examiner* — Katherine M Shi
*Assistant Examiner* — Lindsey Bachman
(74) *Attorney, Agent, or Firm* — Mintz Levin Cohn Ferris Glovsky and Popeo, P.C.

(57) ABSTRACT

Systems and methods are provided for repairing a heart valve, such as a mitral, tricuspid or aortic valve, using an adjustable and removable implant that can be delivered to the heart through the apex in a simplified and non-invasive manner. The implant can include a prosthetic valve portion coupled to a proximal end of a shaft, and an anchor portion coupled to a distal end of the shaft. The prosthetic valve can be suspended within an opening of the heart valve while the anchor portion is affixed to the apex of the heart. When the implant is deployed, a distance between the prosthetic valve portion and the anchor portion can be adjusted, and/or the implant or a portion thereof can be rotated to thereby change the position of the prosthetic valve within the heart valve. This can allow correcting for post-implantation movements of the implant to mitigate potential complications.

19 Claims, 30 Drawing Sheets

Related U.S. Application Data

No. 14/541,601, filed on Nov. 14, 2014, now Pat. No. 9,848,880.

(60) Provisional application No. 61/906,727, filed on Nov. 20, 2013.

(51) Int. Cl.
*A61B 17/00* (2006.01)
*A61F 5/00* (2006.01)
*A61B 17/42* (2006.01)

(52) U.S. Cl.
CPC .......... *A61F 2/2418* (2013.01); *A61F 2/2436* (2013.01); *A61F 2/2457* (2013.01); *A61F 5/0079* (2013.01); *A61B 2017/00247* (2013.01); *A61B 2017/00389* (2013.01); *A61B 2017/00606* (2013.01); *A61B 2017/00623* (2013.01); *A61B 2017/00654* (2013.01); *A61B 2017/00778* (2013.01); *A61B 2017/00986* (2013.01); *A61B 2017/12004* (2013.01); *A61B 2017/12054* (2013.01); *A61B 2017/4233* (2013.01); *A61F 2/2487* (2013.01); *A61F 2220/0008* (2013.01); *A61F 2220/0075* (2013.01); *A61F 2250/001* (2013.01); *A61F 2250/0008* (2013.01); *A61F 2250/0098* (2013.01)

(56) References Cited

U.S. PATENT DOCUMENTS

| | | | |
|---|---|---|---|
| 6,406,420 B1 | 6/2002 | McCarthy et al. | |
| 6,461,320 B1 | 10/2002 | Yencho et al. | |
| 6,942,674 B2 | 9/2005 | Belef et al. | |
| 7,033,373 B2 | 4/2006 | de la Torre et al. | |
| 7,056,333 B2 | 6/2006 | Walshe | |
| 7,625,392 B2 | 12/2009 | Coleman et al. | |
| 7,753,928 B2 | 7/2010 | de la Torre et al. | |
| 8,197,498 B2 | 6/2012 | Coleman et al. | |
| 9,603,600 B2 | 3/2017 | Coleman et al. | |
| 9,848,880 B2 | 12/2017 | Coleman et al. | |
| 9,855,048 B2 | 1/2018 | Coleman et al. | |
| 2002/0055757 A1 | 5/2002 | Torre et al. | |
| 2002/0188170 A1 | 12/2002 | Santamore et al. | |
| 2003/0078604 A1 | 4/2003 | Walshe | |
| 2005/0192615 A1 | 9/2005 | Torre et al. | |
| 2006/0122647 A1 | 6/2006 | Callaghan et al. | |
| 2007/0016287 A1 | 1/2007 | Cartledge et al. | |
| 2007/0185529 A1 | 8/2007 | Coleman et al. | |
| 2007/0270943 A1* | 11/2007 | Solem | A61B 17/0401 623/2.11 |
| 2009/0043153 A1* | 2/2009 | Zollinger | A61B 17/0487 600/37 |
| 2009/0048668 A1 | 2/2009 | Wilson et al. | |
| 2009/0105733 A1 | 4/2009 | Coleman et al. | |
| 2009/0312597 A1 | 12/2009 | Bar et al. | |
| 2010/0114128 A1 | 5/2010 | Coleman et al. | |
| 2010/0298929 A1 | 11/2010 | Thornton et al. | |
| 2011/0040232 A1 | 2/2011 | Magal | |
| 2011/0276091 A1 | 11/2011 | Melanson et al. | |
| 2012/0078360 A1* | 3/2012 | Rafiee | A61F 2/2418 623/2.37 |
| 2012/0197388 A1 | 8/2012 | Khairkhahan et al. | |
| 2012/0316639 A1 | 12/2012 | Kleinschrodt | |
| 2013/0096672 A1* | 4/2013 | Reich | A61F 2/2466 623/2.11 |
| 2013/0165963 A1 | 6/2013 | Coleman et al. | |
| 2013/0172978 A1 | 7/2013 | Vidlund et al. | |
| 2013/0184811 A1 | 7/2013 | Rowe et al. | |
| 2013/0282110 A1 | 10/2013 | Schweich, Jr. et al. | |
| 2014/0214159 A1* | 7/2014 | Vidlund | A61F 2/2409 623/2.14 |
| 2018/0098770 A1 | 4/2018 | Coleman et al. | |
| 2018/0132858 A1 | 5/2018 | Coleman et al. | |

FOREIGN PATENT DOCUMENTS

| | | |
|---|---|---|
| CN | 102470038 A | 5/2012 |
| CN | 102647957 A | 8/2012 |
| CN | 102784018 A | 11/2012 |
| CN | 102824199 A | 12/2012 |
| CN | 103068341 A | 4/2013 |
| CN | 103079498 A | 5/2013 |
| WO | WO-0235980 A2 | 5/2002 |
| WO | WO-2005087140 A1 | 9/2005 |
| WO | WO-2006111961 A2 | 10/2006 |
| WO | WO-2009130619 A1 | 10/2009 |
| WO | WO-2011031981 A1 | 3/2011 |
| WO | WO-2011119101 A1 | 9/2011 |
| WO | WO-2012163820 A2 | 12/2012 |
| WO | WO-2013112450 A1 | 8/2013 |

OTHER PUBLICATIONS

International Search Report and Written Opinion for Application No. PCT/EP2014/075206, dated Feb. 23, 2015 (16 pages).
Chinese Office Action and Search Report for Application No. 201480063220.7, dated Nov. 30, 2016.

\* cited by examiner

ADJUSTABLE HEART VALVE IMPLANT

CROSS-REFERENCE TO RELATED APPLICATIONS

The present application is a continuation of U.S. patent application Ser. No. 15/852,658, filed Dec. 22, 2017, and entitled "Adjustable Heart Valve Implant," which is a continuation of U.S. patent application Ser. No. 14/541,601, filed Nov. 14, 2014, now issued as U.S. Pat. No. 9,848,880, and entitled "Adjustable Heart Valve Implant," which claims priority to U.S. Patent Provisional Application No. 61/906,727, filed Nov. 20, 2013, and entitled "Surgical Implant Devices, Systems, and Methods," each of which is incorporated herein by reference in its entirety.

FIELD

Systems and methods are provided for repairing heart valves using adjustable heart valve implants.

BACKGROUND

A human heart is a vital part of the body having four chambers, the left and right atria and the left and right ventricles. The chambers alternately expand and contract to pump blood through the body. Each chamber of the heart includes a heart valve that, when functioning properly, controls the flow of blood in only one direction through the heart. However, the heart valve can become diseased or otherwise deficient such that it fails to close properly during the contraction of the lower chamber.

Mitral regurgitation is an insufficiency of a mitral valve which occurs when the mitral valve separating the left atrium and the left ventricle does not close properly when the heart pumps out blood. As a result, upon contraction of the left ventricle, blood may abnormally leak (regurgitate) from the left ventricle back into the left atrium, rather than flowing properly to the aorta. Mitral regurgitation can cause dilation of the left-sided heart chambers which, if left untreated, can ultimately lead to potentially fatal heart-rhythm disturbances and heart failure.

Another common heart disorder is aortic insufficiency, such as, for example, aortic stenosis in which the aortic valve located between the left ventricle and the aorta can become abnormally narrowed or constricted (stenotic) and therefore does not open fully. This can decrease the blood flow from the heart and lead to serious heart complications.

Heart valve regurgitation and other heart valve conditions can be caused by a variety of disorders and often require a surgical intervention involving replacement of a natural heart valve or heart replacement. An open heart procedure has been typically performed to surgically repair or replace a diseased or deficient heart valve using, for example, a prosthetic heart valve. However, an open heart surgery has significant risks and can lead to many complications. Moreover, some patients (e.g., children, elderly, patients with chronic conditions, etc.) can be at particular risk for open heart surgery and cannot be treated using this approach.

More recent approaches have been developed that aim at avoiding invasive valve repair or replacement surgeries by delivering a prosthetic valve using a catheter. However, a natural heart valve, such as a mitral valve, has a complicated anatomy and deforms in a complicated manner with the cardiac rhythm. The existing approaches do not adequately mimic the functionality of the mitral valve and may not address such potential issues as, for example, tissue damage, cardiac remodelling and paravalvular leaking. Furthermore, the techniques developed up-to-date may not provide adequate ways for replacing a heart valve implant after its deployment.

Accordingly, there remains a need for improved methods and systems for delivering prosthetic heart valves in a non-invasive manner.

SUMMARY

A method of repairing a mitral valve is provided that in some embodiments includes advancing an outer shaft of an introducer assembly through an apex of a heart into a left atrium of the heart, deploying a prosthetic valve portion of an implant from the outer shaft in the left atrium such that the prosthetic valve portion moves from an unexpanded configuration to an expanded configuration and at least one positioning member on the prosthetic valve portion is disposed on opposite sides of an opening of the mitral valve to suspend the prosthetic valve portion within the opening of the mitral valve, retracting the outer shaft from the left atrium towards the apex of the heart such that an inner shaft of the introducer assembly and at least a portion of an anchor portion of the implant are exposed, and deploying proximal and distal deployable wings on the anchor portion to engage tissue therebetween to removably affix the anchor portion to the apex of the heart. The outer shaft can be advanced through the apex of the heart into the left atrium by directly puncturing the apex of the heart with a leading end of the introducer assembly. Removably affixing the anchor portion to the apex of the heart results in closure of the apex puncture.

The method can vary in any number of ways. In some embodiments, the inner shaft can include an adjustable tether configured to couple the prosthetic valve portion to the anchor portion. The tether can be coupled to the anchor portion using a tether lock. A portion of the tether can be retracted proximal to the proximal end of the anchor portion prior to attaching the tether to the anchor portion using the tether lock. In some embodiments, the tether lock can be recessed into a body of the anchor portion so as not to protrude into the pericardial space. In some embodiments, the tether can be formed of an absorbable or non-absorbable suture. In other embodiments, the tether can include a wire suture (e.g., a metal suture), or it can be formed from any other materials. The tether can have one or more portions.

The method can further include adjusting a distance between the prosthetic valve portion and the anchor portion of the implant. In some embodiments, the distance can be adjusted using the adjustable tether coupling prosthetic valve portion to the anchor portion. The method can also include accessing a proximal end of the anchor portion with an adjustment tool and employing the adjustment tool to adjust the distance. The proximal end of the anchor portion can be accessed percutaneously. The distance can be adjusted by retractably moving the inner shaft with respect to the anchor portion. The length of the inner shaft can be adjusted prior to affixing the anchor portion within the apex of the heart.

In some embodiments, the method can further include rotating a portion of the prosthetic valve portion suspended within the opening of the mitral valve. The method can further additionally or alternatively include rotating the implant when the prosthetic valve portion is suspended within the opening of the mitral valve. The method can further include removing the outer shaft.

In some embodiments, deploying the prosthetic valve portion can include deploying the prosthetic valve portion from the outer shaft in the left atrium, and subsequently retracting the outer shaft from the left atrium to engage the at least one positioning member with the mitral valve.

The prosthetic valve portion of the implant can have any number of variations. For example, in some embodiments, the prosthetic valve portion can include an expandable frame and the at least one positioning member can include an expandable ring circumferentially disposed at an end of the expandable frame. The method can include adjusting a diameter of the expandable frame after the prosthetic valve portion is deployed. In embodiments in which the inner shaft includes an adjustable tether, the diameter of the expandable frame can be adjusted by adjusting a length of the tether or otherwise manipulating the tether.

In some embodiments, the method can further include determining a position of the prosthetic valve portion using at least one radiopaque marker associated with the prosthetic valve portion.

The proximal and distal deployable wings can vary in any number of ways. For example, in some embodiments, the proximal and distal deployable wings can be deployed within tissue of the apex of the heart. In other embodiments, the proximal and distal deployable wings can be deployed at opposite sides of a wall of the apex of the heart. In some embodiments, deploying the proximal and distal deployable wings can include deploying the distal wings and, after the distal wings are deployed, retracting the outer shaft proximally away from the prosthetic valve body to deploy the proximal wings. In some embodiments, the distal wings can be deployed against the wall of the apex of the heart and the proximal wings can be deployed within the tissue. In other embodiments, the proximal wings can be deployed against the wall of the apex of the heart and the distal wings are deployed within the tissue.

In some embodiments, the method can further include mating a proximal end of the anchor portion with an actuator tool, deploying the actuator tool to move the proximal and distal wings from a deployed configuration to an undeployed configuration, advancing the introducer assembly over the actuator tool towards the prosthetic valve portion, deploying the actuator tool to move the prosthetic valve portion from the expanded configuration to the unexpanded configuration, and removing the prosthetic valve portion in the unexpanded configuration from the left atrium through the introducer assembly. The method can further include, after removing the prosthetic valve portion from the introducer sheath, retracting the introducer assembly towards the apex of the heart, inserting a second closure device into the sheath and deploying second proximal and distal wings of a second closure device to engage tissue therebetween at the puncture hole of the apex of the heart.

In other aspects, a method of repairing a heart valve is provided that in some embodiments can include delivering an outer shaft of an introducer assembly through an apex of a heart into an atrium of the heart, deploying a prosthetic valve from the outer shaft in the atrium such that the prosthetic valve moves from an unexpanded configuration to an expanded configuration and at least one positioning member on the prosthetic valve is disposed above an opening of the heart valve to suspend a body of the prosthetic valve within the opening, retracting the outer shaft from the atrium towards the apex of the heart such that the suture tether or inner shaft coupled to and extending between the prosthetic valve and an anchor is exposed, removably affixing the anchor to the apex of the heart, and adjusting a distance between the prosthetic valve and the anchor.

The method can vary in any number of ways. For example, in some embodiments, the inner shaft can include an adjustable tether, such as a flexible suture tether. In such embodiments, the distance between the prosthetic valve and the anchor can be adjusted by altering a length of the tether. For example, the tether can be retracted proximally.

In some embodiments, the method can further include removing the outer shaft through the apex of the heart. In some embodiments, the distance between the prosthetic valve and the anchor can be adjusted after the anchor is affixed to the apex of the heart. Removably affixing the anchor to the apex of the heart can include deploying proximal and distal deployable wings of the anchor to engage tissue therebetween.

The method can further include rotating the body of the prosthetic valve body within the opening of the heart valve. The heart valve can include a mitral valve and the atrium can include a left atrium. The method can further include removing the prosthetic valve from the atrium through the outer shaft.

In yet another aspect, a system for repairing a heart valve is provided that in some embodiments includes an outer shaft and an implant disposed within the outer shaft, the implant including an inner shaft, a prosthetic valve coupled to a distal end of the inner shaft and having a prosthetic valve body and at least one positioning member, the prosthetic valve being configured to be distally advanced from the outer shaft such that the prosthetic valve moves from an unexpanded configuration, and the at least one positioning member being configured to suspend the prosthetic valve within an opening in tissue, and an anchor portion coupled to a proximal end of the inner shaft and configured to be removably affixed to tissue. A distance between the prosthetic valve and the anchor portion can be adjustable.

The system can vary in any number of ways. For example, in some embodiments, the prosthetic valve body can include prosthetic valve leaflets and the at least one positioning member can include at least two arms coupled to the prosthetic valve body. In other embodiments, the prosthetic valve body can include an expandable frame and the at least one positioning member can include an expandable ring circumferentially disposed at a distal end of the expandable frame.

The anchor portion can vary in any number of ways. For example, the anchor portion can include proximal and distal deployable wings configured to engage tissue therebetween.

In yet another aspect, a system for repairing a heart valve is provided that in some embodiments can include an outer shaft and an implant disposed within the outer shaft, the implant including one or more tethers, a prosthetic valve coupled to a distal end of the one or more tethers and having a prosthetic valve body and at least one positioning member, the prosthetic valve being configured to be distally advanced from the outer shaft such that the prosthetic valve moves from an unexpanded configuration, and the at least one positioning member being configured to suspend the prosthetic valve within an opening in tissue, and an anchor portion coupled to a proximal end of the one or more tethers and configured to be removably affixed to tissue. A distance between the prosthetic valve and the anchor portion can be adjustable.

The system can vary in any number of ways. For example, the one or more tethers can be flexible tethers. The flexible tethers can be formed from a suture. In some embodiments, the prosthetic valve body includes prosthetic valve leaflets and the at least one positioning member can include at least two arms coupled to the prosthetic valve body. In other embodiments, the prosthetic valve body includes an expandable frame and the at least one positioning member can include an expandable ring circumferentially disposed at a distal end of the expandable frame.

The anchor portion can vary in any number of ways. For example, the anchor portion can include proximal and distal deployable wings configured to engage tissue therebetween.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. Further, the features illustrated or described in connection with one exemplary embodiment may be combined with the features of other embodiments. Such modifications and variations are intended to be included within the scope of the present invention.

Methods and devices are provided for repairing and replacing heart valves. In particular, the described techniques utilize a system for delivering an adjustable implant into a heart valve that includes a prosthetic valve portion configured to be positioned within an opening of a natural heart valve, such as a mitral valve, a tricuspid valve, or an aortic valve, and an anchor portion configured to secure the implant to an apex of the heart. The prosthetic valve can have a configuration that allows it to be removably suspended within an opening of a diseased or defective heart valve such that the prosthetic valve can repair abnormalities of the heart valve or completely replace the diseased valve.

In certain exemplary methods, the implant can be delivered to the heart valve through the apex of the heart. The transapical delivery allows delivering the implant in a minimally invasive manner, for example, percutaneously, which may allow high risk patients to be treated. In some cases, even a relatively non-invasive minithoracotomy procedure can be avoided. No additional sutures (e.g., purse-string sutures) are required to be placed in the apex, which can reduce trauma to cardiac tissue and thus decrease a risk of complications.

Furthermore, after the implant has been deployed within the heart, a distance between the prosthetic valve portion and anchor portion can be adjusted. In some embodiments, the implant or a portion thereof can be rotated. The adjustment can be performed in a non-invasive or minimally invasive manner and can allow reducing or eliminating potential post-implantation complications such as, for example paravalvular leaks, cardiac remodelling (undesirable structural modifications of tissue) and other potential conditions, without removing the implant from the implantation site. The deployed implant can be moved to an undeployed configuration and removed from the implantation site in a simple manner. Accordingly, the implant placement procedure in accordance with the described embodiments can be simple, repeatable, cost-effective, and it causes less discomfort to a patient.

Figure 1A:
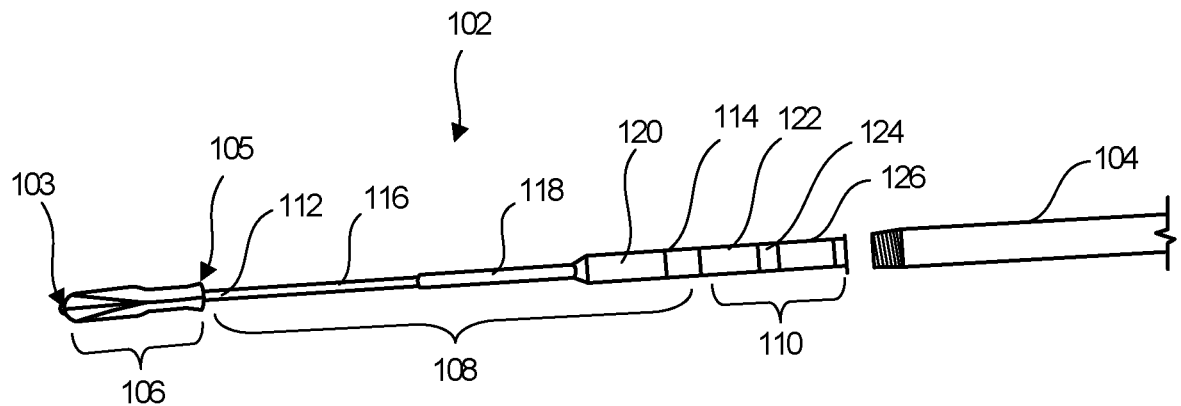
FIG. 1A is a side view of an implant in accordance with some embodiments having a prosthetic valve portion in an undeployed configuration.
Figure 1B:
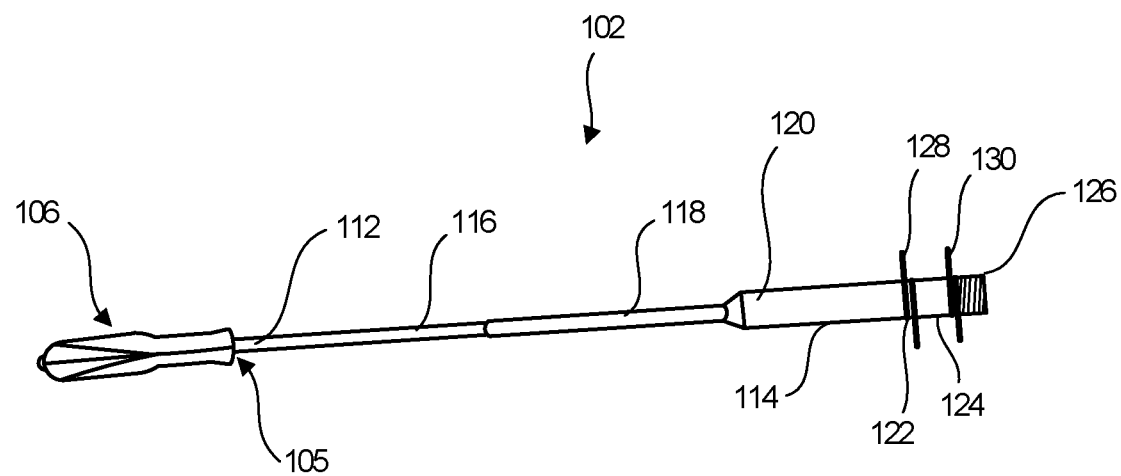
FIG. 1B is a side view of the implant of FIG. 1A having proximal and distal wings deployed.

FIGS. 1A and 1B illustrate a system 100 for repairing a heart valve in accordance with one embodiment. The system 100 may include an implant 102 and an outer shaft 104 which can define a lumen extending therethrough configured to slidably receive the implant 102 therein. The outer shaft 104 can be a part of the introducer assembly configured to deliver the implant 102 into the heart. The outer shaft 104 is shown in FIG. 1A by way of example as a component separate from the implant 102, to illustrate that the outer shaft 104 is configured to removably receive the implant 102. The outer shaft 104 can be an elongate tubular member configured to be inserted into a heart through the apex.

As shown in FIG. 1A, the implant 102 can include a prosthetic valve portion 106, an inner shaft 108, and an anchor portion 110. The prosthetic valve portion 106 can be coupled at a proximal end 105 thereof to a distal end 112 of the inner shaft 108, and the anchor portion 110 can be coupled to a proximal end 114 of the inner shaft 108. As used herein, the term "proximal" end or portion refers to an end or portion that is nearest to a person operating the outer shaft 106 (e.g., using a suitable actuator tool), and the term "distal" end or portion refers to an end or portion that is closer to a forward end 103 of the implant 102.

In the illustrated embodiment, the inner shaft 108 can have distal, middle, and proximal portions 116, 118, 120, which can be configured to slidably and fixedly mate with each other. For example, at least a portion of the distal portion 116 can be configured to be slidably received within the middle portion 118. In some embodiments, as discussed in more detail below, the inner shaft 108 can be formed from an absorbable or non-absorbable suture extending between the prosthetic valve portion 106 and the anchor portion 110. The suture may further extend through the anchor portion 110. In some embodiments, at least a portion of the middle portion 118 of the inner shaft 108 can be configured to be slidably received within the proximal portion 120. In this way, a distance between the distal and proximal ends 112, 114 of the inner shaft 108 can be adjustable. A screw mechanism or any other suitable mechanism can be used to adjust a length of the inner shaft 108. The proximal portion 120 of the inner shaft 108 can be configured to mate on an inner surface thereof with a suitable tool that can be manipulated to adjust the length of the inner shaft 108.

In some embodiments, a diameter of the proximal portion 120 can be larger than diameter(s) of the distal and middle portions 116, 118. The distal and middle portions 116, 118 can have diameter(s) that are appropriate for implantation within a chamber of the heart. The anchor portion 110 can be sized appropriately so as to close a hole or puncture in the apex of the heart. In the illustrated embodiment, the proximal portion 120 is mated with the anchor portion 110 and is the same or similar in size (e.g., diameter) to the anchor portion 110. However, in other embodiments, the diameter of the proximal portion 120 can be smaller than that of the anchor portion 110. The distal, middle, and proximal portions 116, 118, 120 can have any suitable lengths. In some embodiments, one or more portions of the inner shaft 108 can be rotatable with respect to other portions. For example, the distal and middle portions 116, 118 can be configured to be able to rotate with respect to the proximal portion 120. This can allow adjusting the implant 102 by rotating the prosthetic valve 106 or the entire implant 102 after it has been deployed. A person skilled in the art will appreciate that the inner shaft 108 can have various configurations and can include any number of components, as the embodiments described herein are not limited in this respect.

The anchor portion, which is configured to function as a closure device used for closing a hole or puncture in tissue, can also have a variety of configurations. As shown in FIG. 1A, the anchor portion 110 can include distal, middle, and proximal portions 122, 124, 126. The distal portion 122 of the anchor portion 110 can be coupled to the proximal end 114 of the inner shaft 108. The distal and proximal portions 122, 126 of the anchor portion 110 can be configured to expand to form deployable wings 128, 130 shown in FIG. 1B. The deployed wings 128, 130 can be maintained in the expanded configuration until the anchor portion 110 is manipulated to cause the wings 128, 130 to collapse to the undeployed configuration. It should be appreciated that the implant 102 can include any other components not shown herein that are configured such that the anchor portion 110 can reversibly form the wings 128, 130.

In some embodiments, which are discussed in more detail below, the inner shaft 108 can include one or more adjustable tethers (e.g., suture or suture-like tether(s)) extending between the prosthetic valve portion and the anchor portion.

In such embodiments, the implant 102 can additionally or alternatively include components to provide a tether lock or clamp. This lock can be used to reversibly couple the one or more tethers to the implant 102 following adjustment of a length of the tether(s).

In some embodiments, the implant 102 can include components configured as described at least in U.S. Pat. No. 7,625,392 entitled "Wound closure devices and methods," issued Dec. 1, 2009, U.S. Pat. No. 8,197,498 entitled "Gastric bypass devices and procedures," issued Jun. 12, 2012, U.S. Patent Application Publication No. 2009/0105733, entitled "Anastomosis devices and methods," filed Oct. 22, 2007, and U.S. Patent Application Publication No. 2013/0165963, entitled "Devices and methods for occluding or promoting fluid flow," filed Dec. 21, 2011, the contents of each of which are incorporated herein by reference in their entireties.

The prosthetic valve portion 106 can also have a variety of configurations that allow it to be inserted into a heart through the outer shaft 104. For example, the prosthetic valve 106 can be configured such that it can move between unexpanded and expanded configurations. In FIGS. 1A and 1B, the prosthetic valve portion 106 is shown in the unexpanded configuration.

Figure 2A:
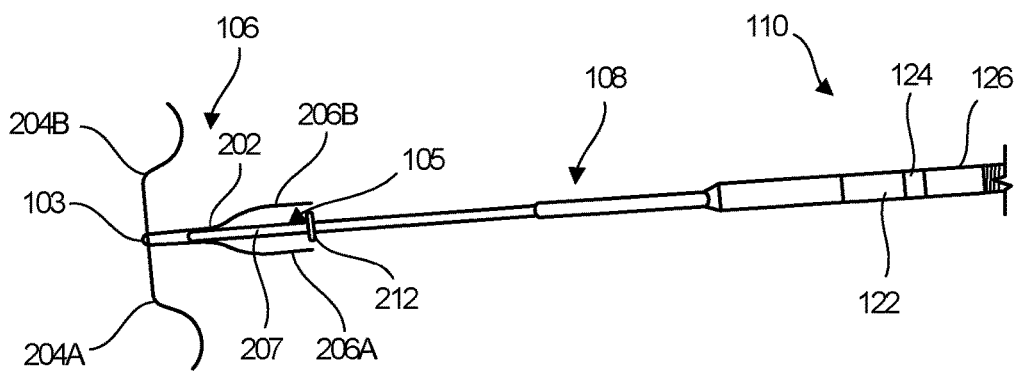
FIG. 2A is a side view of the implant of FIGS. 1A and 1B having the prosthetic valve portion in a deployed configuration.
Figure 2B:
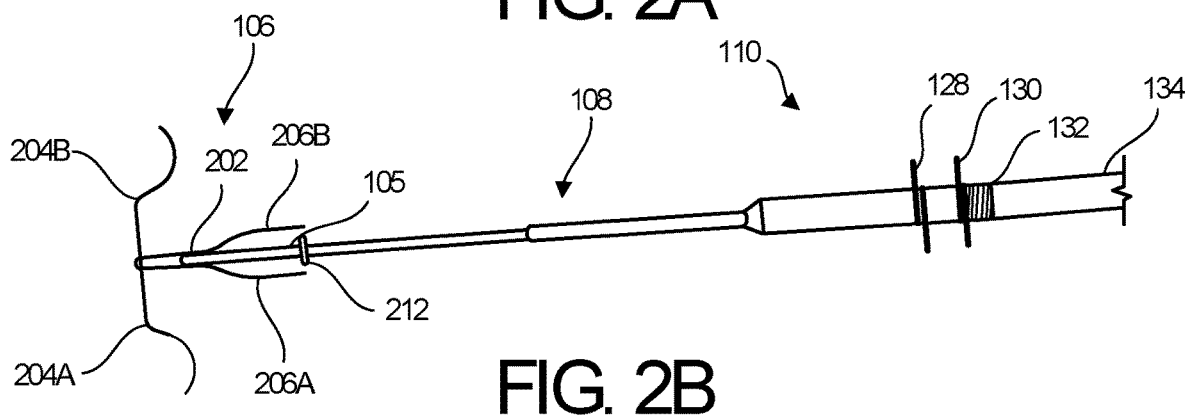
FIG. 2B is a side view of the implant of FIG. 2A having proximal and distal wings deployed.

An embodiment of the prosthetic valve portion 106 in the expanded configuration is shown in more detail in FIGS. 2A and 2B. FIG. 2A shows the implant 102 with the wings 128, 130 undeployed, whereas FIG. 2B shows an example with the wings 128, 130 of the implant 102 deployed. As schematically shown in FIG. 2B, a proximal end 132 of the anchor portion 110 can be configured to mate with an actuator tool 134 that can be used to manipulate the inner shaft 108 to adjust a length thereof. The same or different tool can be configured to mate with the anchor portion 110 through its proximal end 132 to deploy the wings 128, 130. Moreover, a suitable actuator tool can be mated with the anchor portion 110 to cause the deployed wings 128, 130 to revert to the undeployed configuration.

In some embodiments, the prosthetic valve portion can include a prosthetic valve body and at least one positioning member configured to suspend the prosthetic valve portion within an opening of a heart valve. As shown in FIGS. 2A and 2B, the prosthetic valve portion 106 can include a valve body 202 and positioning members 204A, 204B coupled thereto. In this example, the positioning members 204A, 204B can be in the form of positioning arms extending in opposite directions from the valve body 202. The prosthetic valve portion 106 can also include a valve shaft 207 extending between the proximal end 105 of the prosthetic valve portion 106 and the distal tip 103 of the implant 102.

Figure 3:
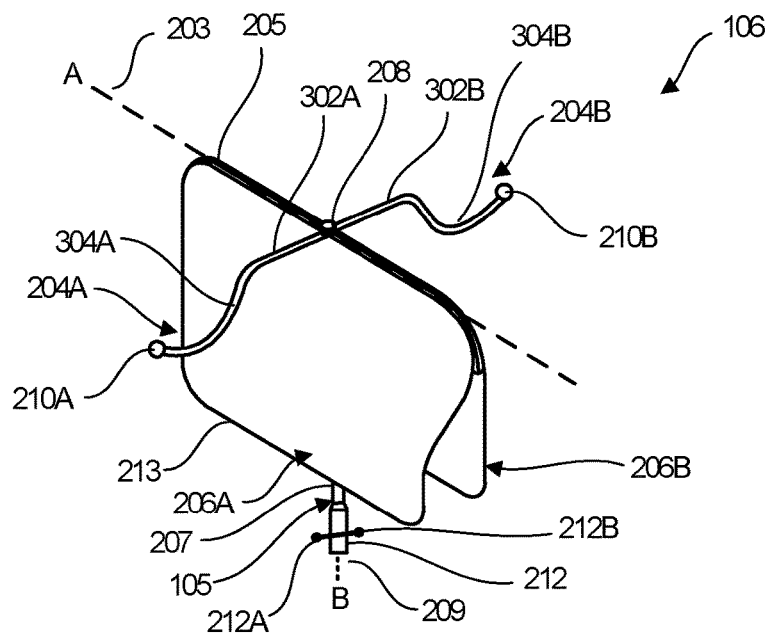
FIG. 3 is a schematic illustration of an enlarged view of a prosthetic valve portion in accordance with some embodiments.

As shown in FIG. 3 illustrating an enlarged view of the prosthetic valve body portion 106, the valve body 202 can include a spine 205 coupled to the distal end 112 of the inner shaft 108 and leaflets 206A, 206B hingeably coupled to the spine 205. The leaflets 206A, 206B can be flexibly coupled to the spine 205 such that they can pivot or flap with respect to the spine 205 as the heart contracts and relaxes. In some embodiments, the leaflets 206A, 206B can come together at one end to form a spine such that opposite ends of the leaflets can be configured to pivot or flap with respect to the spine. The leaflets 206A, 206B can have any suitable dimensions that allow them to mimic the function of a native heart valve. The leaflets 206A, 206B, which can be elastic, can be made from any suitable biological or synthetic material, or any combination thereof.

The prosthetic valve portion 106, when deployed within the heart, can move from the unexpanded configuration to the expanded configuration. In some embodiments, the valve body 202 having the positioning members 204A, 204B and leaflets 206A, 206B coupled thereto can slide over the valve shaft 207 such that the positioning members 204A, 204B and leaflets 206A, 206B can fold and unfold in an umbrella-like fashion. For example, in the unexpanded configuration, a member 212 located at the proximal end 105 of the prosthetic portion 106 can be pushed in any suitable manner (e.g., by an outer shaft used to insert the implant to the implantation site, discussed below) which can cause the leaflets 206A, 206B and positioning members 204A, 204B to move outward and thus unfold. Similarly, when the prosthetic valve portion 106 is in the expanded configuration, the member 212 can be pushed or otherwise actuated (e.g., pulled) depending on its configuration to cause the positioning members 204A, 204B and leaflets 206A, 206A to move inward and fold.

The prosthetic value portion 106 can be used to mitigate abnormalities of a diseased heart valve and/or it can entirely replace the natural heart valve by mimicking operation of the valve. For example, when the implant 102 is used to repair a diseased mitral valve, as the left ventricle contracts (ejecting oxygen-rich blood throughout the body) and a healthy mitral valve would close, the leaflets 206A, 206B can be spaced apart with respect to the longitudinal axis B 209 of the implant 102 to ensure a proper closure of the diseased mitral valve to thereby prevent an undesirable backflow of blood (regurgitation) into the left atrium. When the left ventricle relaxes and the mitral valve opens to allow the blood to flow from the left atrium to the left ventricle, the leaflets 206A, 206B can be maintained close together without interfering with the blood flow.

The positioning members 204A, 204B can be coupled to the spine 205. For example, in some embodiments, the positioning members 204A, 204B can be formed integrally with the spine 205. However, it should be appreciated that the positioning members 204A, 204B can be coupled to the spine 205 or other portion of the prosthetic valve portion 106 in any suitable manner, as embodiments are not limited in this respect.

The positioning members 204A, 204B can have any suitable configuration. For example, the positioning members 204A, 204B can be formed from one or more elongate wires having a shape that allows the positioning members 204A, 204B to retain the prosthetic valve portion 106 within a mitral valve. In one embodiment, as shown in FIG. 3, each of the positioning members 204A, 204B can form a shoulder having a straight or flat portion (302A, 302B) extending from and coupled to the spine 205 and a curved portion (304A, 304B) coupled to the flat portion (302A, 302B). The straight or flat portions 302A, 302B can be formed from separate wires or other elements, or, in some cases, they can be formed from the same element (e.g., wire or other material(s)). Each of the portions 302A, 302B can be coupled to the spine 205 at the portion 208 thereof, at shown in FIG. 3. It should be appreciated that the portions 302A, 302B may not necessarily be straight or flat along their entire lengths and can have other suitable shapes.

In the example of FIG. 3, the curved portions 304A, 304B can be half-U-shaped portions coupled to the portions 302A, 302B at tops of the "half-Us" formed by the curved portions 304A, 304B. In some embodiments, the curved portions 304A, 304B can be integrally formed with the flat portions 302A, 302B. FIG. 3 shows the curved portions 304A, 304B that are curved outwardly away from the longitudinal axis B 209 of the implant 102. However, other configurations of the curved portions 304A, 304B can be utilized as well. The positioning members 204A, 204B or part(s) thereof (e.g., curved portions 304A, 304B) can be at least partially flexible to accommodate anatomical features of an annulus of a heart valve which the positioning members 204A, 204B are configured to engage. The length of the positioning members 204A, 204B can correspond to the diameter of the annulus of the heart valve such that the members 204A, 204B extend beyond the valve opening.

In some embodiments, the positioning members 204A, 204B can have suitable features configured to facilitate engaging tissue above the opening of the heart valve. However, regardless of a specific configuration of the positioning members 204A, 204B, they can be configured to engage the tissue in an atraumatic manner to decrease or eliminate damage to the tissue.

As shown in FIG. 3, when the prosthetic valve portion 106 is in the expanded configuration, the positioning members 204A, 204B can be configured to extend in the opposite directions from the portion 208 of the spine 205 along an axis that is perpendicular or approximately perpendicular to a longitudinal axis A (indicated by a numerical reference 203 in FIG. 3) of the spine 205. It should be appreciated that the positioning members 204A, 204B can have any suitable shape that allows them to suspend the prosthetic valve portion 106 within a heart valve, and the shape of the positioning members 204A, 204B in FIGS. 2A, 2B, and FIG. 3 is shown by way of example only. Furthermore, in some embodiments, the prosthetic valve portion can include more than two positioning members having any suitable configuration. For example, in some embodiments, additional positioning members similar to the members 204A, 204B can extend from the spine 205 in the same plane at the members 204A, 204B, at different angles from the members 204A, 204B. In addition, in some embodiments, a single positioning member can be employed.

Regardless of the specific configuration of the positioning members 204A, 204B and the way in which they are coupled to the spine 205, the positioning members 204A, 204B can be foldably coupled to the spine 205 such that, when the prosthetic valve portion 106 moves from the unexpanded configuration to the expanded configuration (e.g., when the implant 102 is deployed), the positioning members 204A, 204B can be unfolded to extend at the opposite sides of the valve body 202 as shown in FIGS. 2A, 2B and 3. When the prosthetic valve portion 106 moves from the expanded configuration to the unexpanded configuration (e.g., when the implant 102 is undeployed to be subsequently removed from the implantation site) shown in FIGS. 1A and 1B, the positioning members 204A, 204B can be folded such that they extend along the sides of the leaflets 206A, 206B which can also be configured to be folded in the undeployed position. In some embodiments, one or more portions of the prosthetic valve portion 106 can be stretchable such that the prosthetic valve portion 106 in the expanded configuration, when pulled proximally, can collapse like an umbrella.

In some embodiments, the implant (e.g., one or more positioning members and/or other elements of the implant) can have associated therewith one or more markers that may be used to determine a location of the prosthetic valve portion within the heart in a non-invasive manner. The markers can be useful to ensure proper positioning of the prosthetic valve portion during delivering of the implant into the heart and when the position of the prosthetic valve portion or the entire implant is adjusted. The markers can be radiopaque elements (e.g., made from platinum, gold, silver, tungsten, or tantalum) having any suitable shape and size (e.g., rings or other elements) that are visible using ultrasound, X-ray, computed tomography (CT) or any other suitable imaging technique. However, it should be appreciated that any other suitable types of markers can be utilized, including, in some cases, radiolucent markers.

FIG. 3 shows that the prosthetic valve portion 106 can include markers 210A, 210B on ends of positioning members 204A, 204B. A member 212 located at the proximal end 105 of the prosthetic portion 106 can also have coupled thereto markers 212A and 212B. Additionally or alternatively, one or both of the leaflets 206A, 206B can have markers coupled thereto. In FIG. 3, a marker 213 coupled to an edge of the leaflet 206A is shown by way of example. It should be appreciated, however, that one or more markers can be coupled to one or both leaflets 206A, 206B at any location on a surface thereof. Furthermore, in some embodiments, a part or the entire area of the spine 205 or other portion of the prosthetic valve 106 can be radiopaque or otherwise detectable using various imaging techniques to additionally facilitate the determination of the location of the prosthetic valve.

The manner in which the markers are positioned can depend on a configuration of the prosthetic valve portion and any other factors. Regardless of the way in which the markers of a suitable size and shape are positioned on one or more portions of the implant described herein, the markers can be used to track a position of the implant and/or portions thereof when the implant is in use. Furthermore, in some embodiments, the markers may be omitted, and the position of the implant can be determined in any suitable manner, as embodiments described herein are not limited in this respect.

Figure 4A:
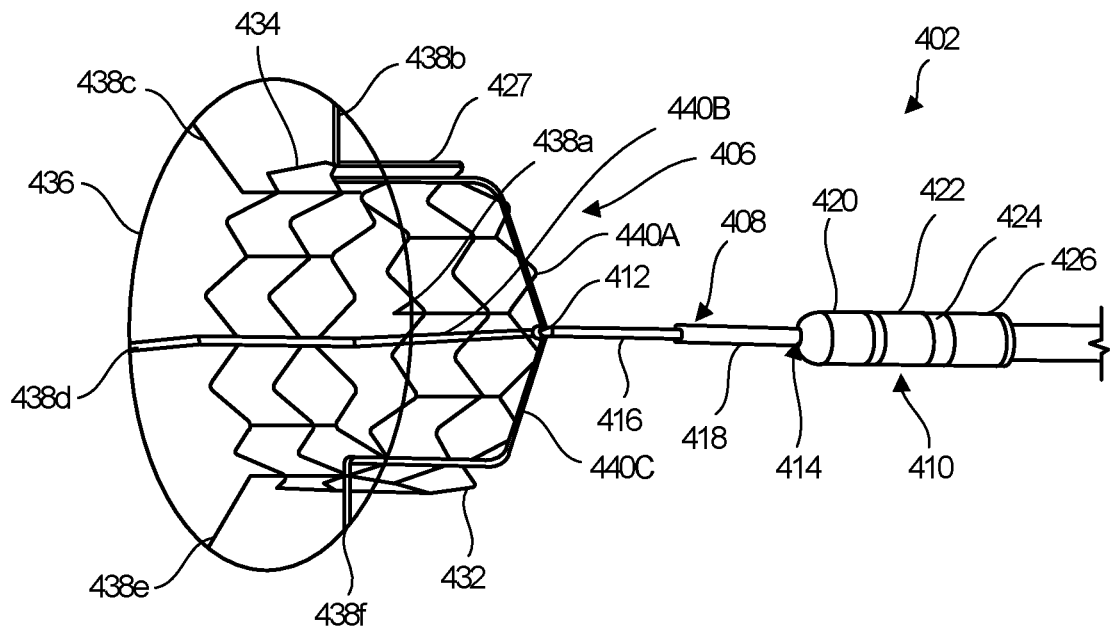
FIG. 4A is a side perspective view of an implant in accordance with some embodiments.
Figure 4B:
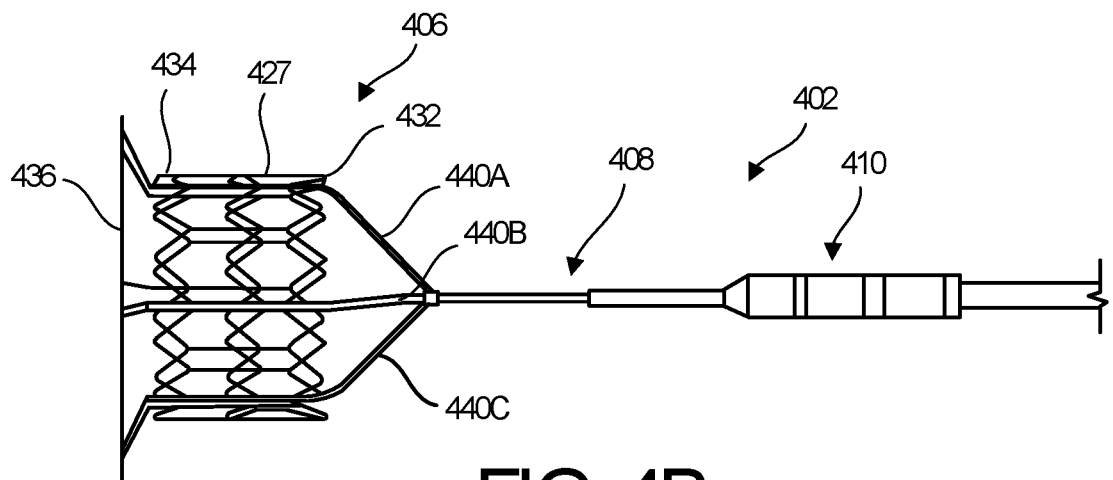
FIG. 4B is a side view of the implant of FIG. 4A.
Figure 4C:
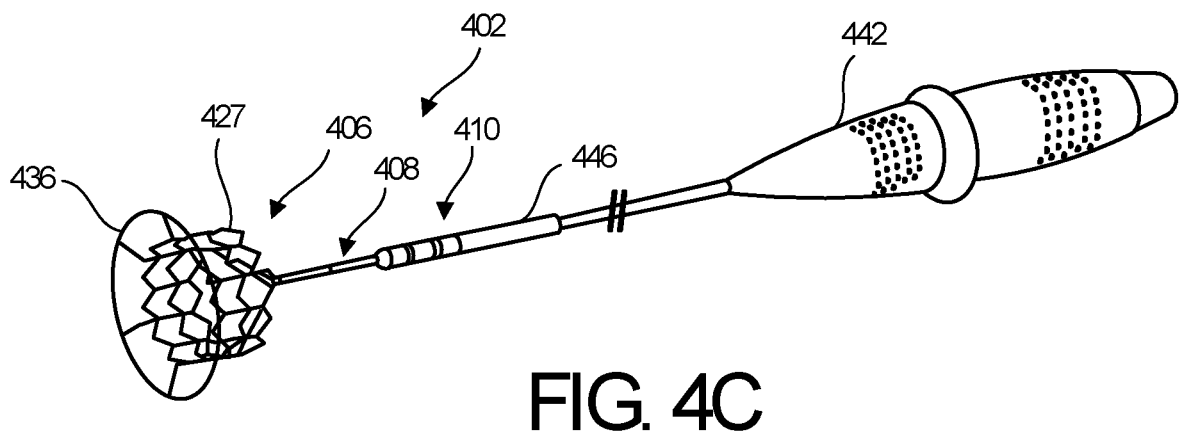
FIG. 4C is a side perspective view of the implant of FIG. 4A showing the implant coupled to an actuator tool, in accordance with some embodiments.

The implants in accordance with some embodiments can include a prosthetic valve portion having any suitable configuration. For example, in some embodiments, as shown in FIGS. 4A, 4B and 4C, an implant 402 can include a prosthetic valve portion 406 including a valve body 427 comprising an expandable/collapsible frame. The frame 427 can have proximal and distal portions 432, 434, with the proximal portion 432 coupled to a distal end 412 of an inner shaft 408 having distal and proximal ends 412, 414. The inner shaft 408 can have a distal portion 416, a middle portion 418, and a proximal portion 420 coupled to an anchor portion 410. In some embodiments, the inner shaft 408 can be configured as one or more tethers (e.g., formed from one or more sutures) that extend between the distal end of the prosthetic valve portion 406 and the anchor portion 410. The tethers can be slidably connected to the anchor portion 410, e.g., via a locking component coupled to the anchor 410, to allow adjusting a distance between the prosthetic valve portion 406 and the anchor portion 410 by adjusting a length of the tethers.

Figure 5A:
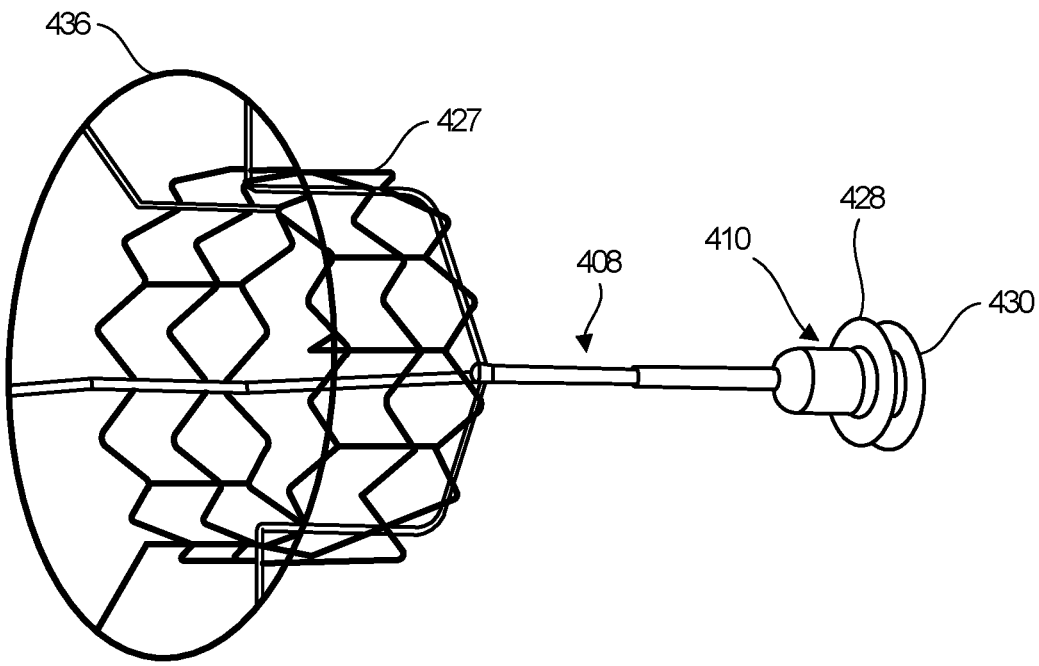
FIG. 5A is a side perspective view of the implant of FIG. 4A showing deployable wings.
Figure 5B:
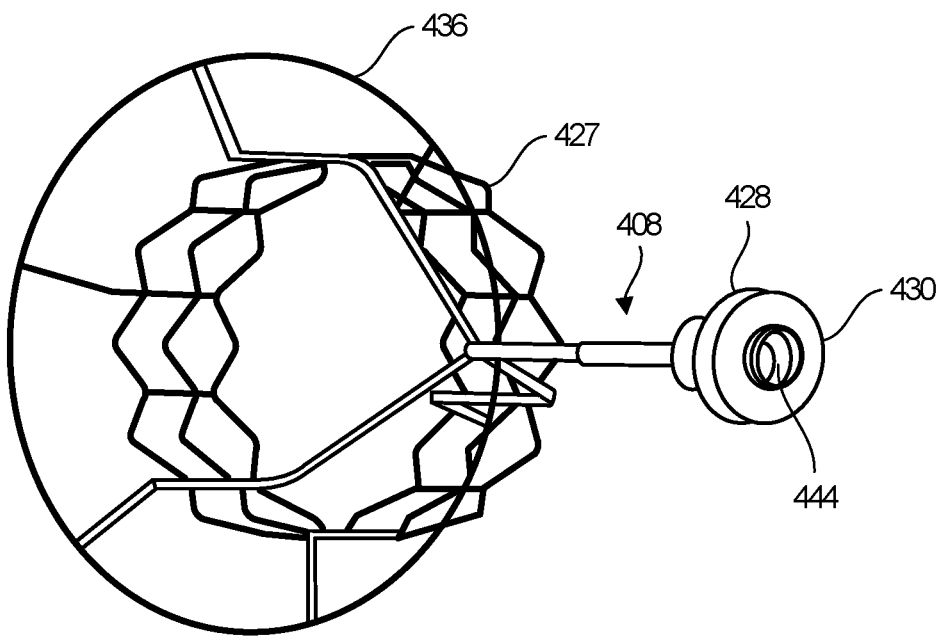
FIG. 5B is another side perspective view of the implant of FIG. 4A showing deployable wings.

Similar to anchor portion 110 shown in FIGS. 1A and 1B, the anchor portion 410 may include distal, middle, and proximal portions 422, 424, 426, and the distal and proximal portions 422, 426 can be configured to expand to form deployable wings 428, 430 shown in FIGS. 5A and 5B. The deployable wings 428, 430 can be configured to form similar to the deployable wings 128, 130, as shown in FIG. 1B.

As shown in FIGS. 4A to 4C, the prosthetic valve portion 406 can have a positioning member 436 configured as a ring circumferentially coupled to the distal portion 434 of the valve body 427. The positioning member 436 can be coupled to the valve body 427 via legs 438a-438f which can be bent, as shown in FIGS. 4A-4C, so that the prosthetic valve portion 406 conforms to the geometry and function of a native heart halve. It should be appreciated that six legs 438a-438f are shown by way of example only, as any suitable number of structural features of any suitable type can be used to couple the positioning member 436 to the valve body 427.

It should also be appreciated that the positioning member 436 can be formed integrally with the valve body 427. The positioning member 436 can have a configuration different from a ring and can additionally or alternatively include any number of features. For example, the positioning member 436 can have multiple features disposed circumferentially around the distal portion 434 of the valve body 427. In some embodiments (e.g., in which the positioning member 436 is formed integrally with the valve body 427), the positioning member 436 can be formed from the same elements or segments as those used to form the valve body 427. The positioning member 436 can be formed from elements that can terminate at a distal-most end of the member 436 as a ring or as multiple structures having any suitable shape(s).

In some embodiments, the prosthetic valve portion 406 can include an insert (not shown) positioned inside a portion or an entire area of the valve body 427 and/or the positioning member 436. The insert can be positioned so that it lines the interior of the valve portion 406 and can be used to provide additional integrity to the structure of the prosthetic valve portion 406 when it is in use. The insert can be formed from any suitable material. For example, the insert can be formed from a natural material, such as bovine and/or porcine pericardial tissue. Additionally or alternatively, the insert can be formed from a synthetic material, such as polytetrafluoroethylene (PTFE), polyethylene terephthalate (PET), or any other suitable material(s).

The valve body 427 can be mated to the inner shaft 408 via struts 440A, 440B, 440C shown in FIGS. 4A and 4B. It should be appreciated, however, that the valve body 427 can be mated to the inner shaft 408 using any number of any other structural elements. As shown in FIGS. 4A and 4B, the distal end 412 of the inner shaft 408 can be configured to function as a junction of the struts 440A, 440B, 440C where the struts 440A, 440B, 440C are attached to the inner shaft 408. The 440A, 440B, 440C can be attached to the junction fixedly or flexibly. For example, in some embodiments, the junction can be configured as a swivel joint or other similar mechanism that allows the valve body 427 to swivel or otherwise move in any direction with respect to the junction, without disturbing or changing the orientation of the inner shaft 408 and the anchor portion 410 to which it is attached.

The prosthetic valve portion 406 can be self-expanding or expandable using an additional device such that, in a pre-deployed configuration, a diameter of the prosthetic valve portion 406 allows it to be inserted into an outer shaft of an introducer assembly (not shown in FIGS. 4A-4C) and delivered through the outer shaft into an area of the heart (e.g., an atrium). When deployed, the prosthetic valve portion 406 can expand radially away from the distal end 412 of the inner shaft 408 and reversibly self-lock to remain in the expanded configuration to fit the geometry of the heart valve. Prosthetic valve portion 406 can be configured to expand in a manner that prevents its upward and downward migration when the valve 406 is suspended within the opening of the mitral valve. When deployed, the prosthetic valve portion 406 can expand and contract such that its diameter and the overall configuration change to adapt to the dynamic geometric environment of the heart valve (e.g., a mitral valve) as the heart pumps blood.

The positioning member 436 can be configured to be expandable in any suitable manner. For example, portions of the ring-shaped positioning member 436 between sites of attachment of legs 438a-438f can telescopically slide over each other such that the positioning member 436 can expand and contract. Regardless of its specific geometry and a wire pattern, the prosthetic valve portion 406 can be configured to expand and collapse in respective deployed and undeployed configurations.

Although not shown in FIGS. 4-5, in some embodiments, the prosthetic valve portion 406 or any other portion(s) of the implant 402 can include one or more markers that can help determine a position of, for example, the prosthetic valve portion 406, and can therefore be used for guiding a cardiac surgeon/cardiologist through delivery, deployment, adjustment and/or removal of the implant 402. Similarly to the markers described in connection with the prosthetic valve portion 106, the markers positioned on the implant 402 can be radiopaque markers or markers otherwise detectable using any suitable imaging technique. The markers can have any suitable size and shape and can be positioned on the implant 402 in any suitable manner.

It should be appreciated that a specific wire pattern of the valve body 427 comprising two rows of hexagonal elements is shown in the embodiment of FIGS. 4A-4C by way of example only. The frame can be formed from any number of any suitable circular, oval, ellipsoidal, or any other types of elements or segments which can form any regular or irregular patterns.

The prosthetic valve portion in accordance with the described techniques can be flexible and it can maintain its structural integrity which allows it to be ergonomic, conform to the structure of a native heart valve, and mimic operation of the native valve. The prosthetic valve portion can have any suitable configuration which can depend on the anatomy of a heart valve, such as a mitral valve, a tricuspid valve, or an aortic valve. The prosthetic valve portion can be formed from stainless steel, Nitinol®, or other biocompatible material(s). For example, Cu—Al—Ni alloys or other shape memory alloys can be used. The prosthetic valve portion can also be formed from polymer(s). In some embodiments, one or more elements of the prosthetic valve portion can be flexible that allows the prosthetic valve portion to adapt to the dynamic geometric environment of the heart valve.

In some embodiments, the prosthetic valve portion can be configured such that it can be suspended within a heart valve using one or more positioning members, with or without penetrating tissue. In the example illustrated in connection with FIGS. 4A to 4C, the positioning member 436 can be configured to engage with an annulus of a heart valve such that the positioning member 436 is disposed above an opening of the valve and the valve body 427 is suspended within the opening. The positioning member 436 can be configured to withstand dislodgment forces that can be exerted thereon (e.g., during systole) and to thereby maintain a proper position and reduce risks of migration of the valve body 427 suspended within an opening of the natural heart valve (e.g., the mitral valve).

As shown in FIG. 4C, the anchor portion 410 of the implant, which can be positioned within the apex of the heart when the implant 402 is inserted into the heart, can be removably mated with an actuator 442 which can be used to urge the deployable wings 428, 430 (shown in FIGS. 5A and 5B) to be deployed. FIG. 5A illustrates the implant 402 with the wings 428, 430 deployed to engage tissue therebetween. FIG. 5B additionally illustrates that a proximal end of the anchor portion 410 can have a mating feature 444 for engaging a distal end 446 (FIG. 4C) of the actuator 442 or other instrument.

As mentioned above, in some embodiments, an inner shaft of the implant can include a tether portion having one or more tethers extending between a prosthetic valve portion and an anchor portion. The tether portion can be coupled to the anchor portion using a tether lock or clamp which can be any locking element. A proximal end of one or more tethers can be retracted proximal to the proximal end of the anchor portion prior to coupling the tethers to the anchor portion using the tether lock. In some embodiments, the tether portion is formed from an absorbable or non-absorbable material, such as, for example, suture. The tether portion can be formed from a suitable metal material and can be a wire suture (e.g., a metal suture). One skilled in the art will appreciate that the tether portion can include any number of tethers formed from any suitable material(s).

FIGS. 5C-5H illustrate examples of implants and a method of their use in accordance with embodiments in which the inner shaft is formed by one or more tethers.

Figure 5C:
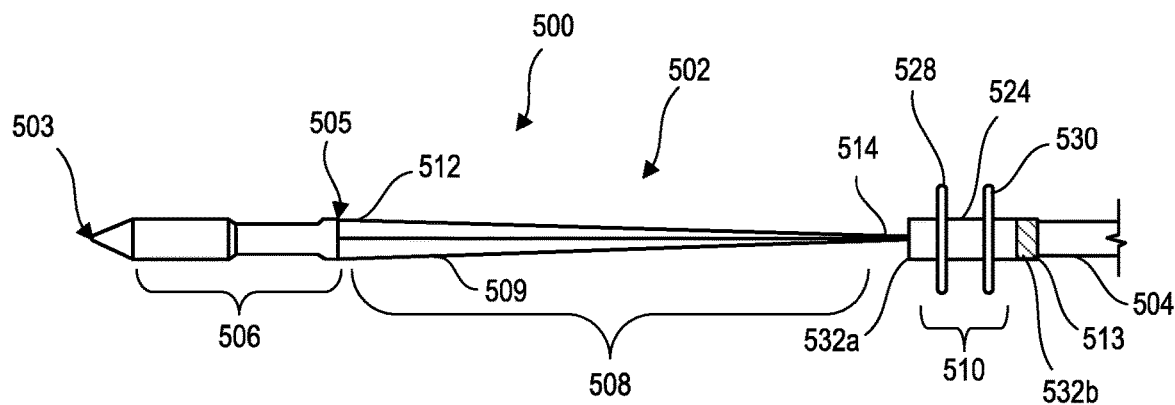
FIG. 5C is a side view of an implant in accordance with some embodiments having a prosthetic valve portion in an undeployed configuration and proximal and distal wings deployed.

FIGS. 5C to 5F illustrate a system 500 for repairing a heart valve in accordance with some embodiments. As shown in FIG. 5C, the system 500 may include an implant 502 and an outer shaft 504 which can define a lumen extending therethrough configured to slidably receive the implant 502 therein. Similar to outer shaft 104 (FIG. 1A), the outer shaft 504 can be a part of an introducer assembly configured to deliver the implant 502 into the heart.

As shown in FIG. 5C, the implant 502 can include a prosthetic valve portion 506, a tether portion 508, and an anchor portion 510. The prosthetic valve portion 506 can be coupled at a proximal end 505 thereof to a distal end 512 of the tether portion 508, and the anchor portion 510 can be coupled to a proximal end 514 of the tether portion 508.

Figure 5D:
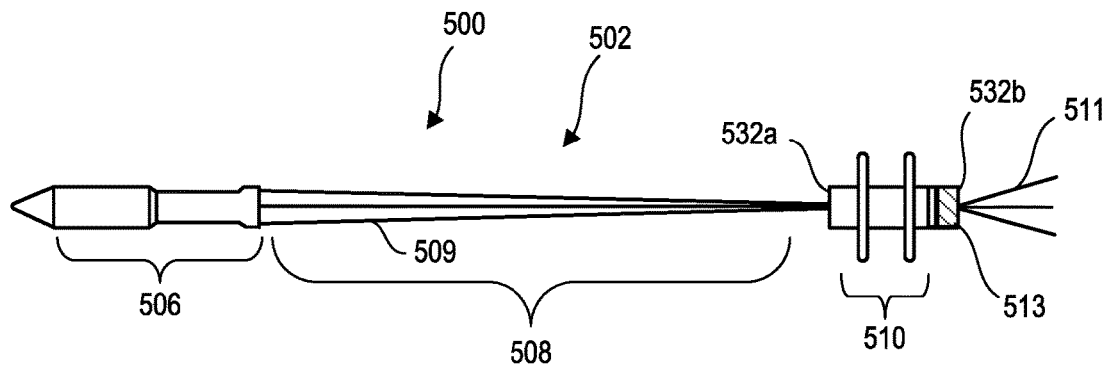
FIG. 5D is another side view of the implant of FIG. 5C.
Figure 5E:
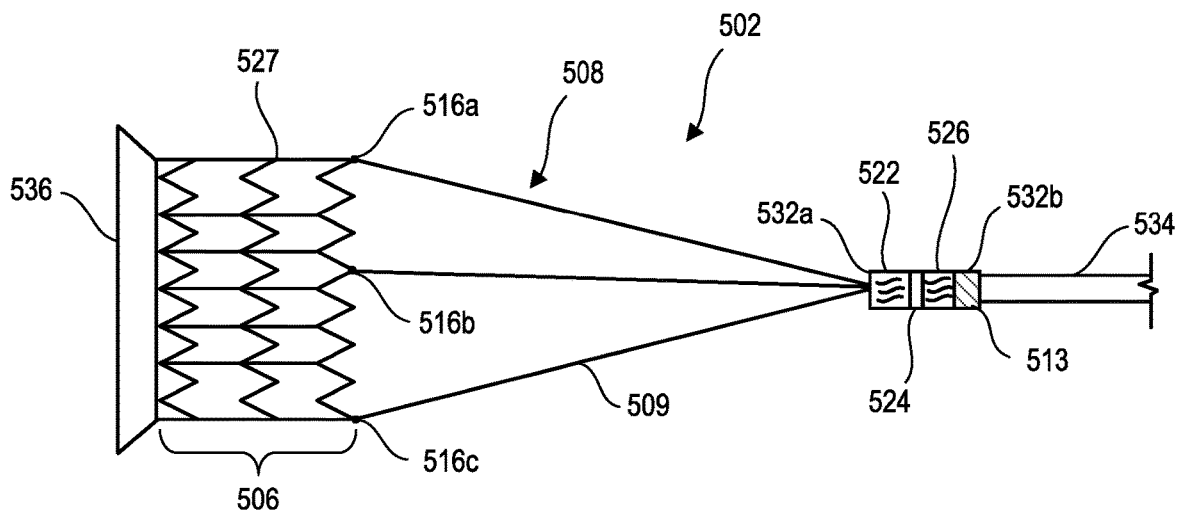
FIG. 5E is another side view of the implant of FIG. 5C having the prosthetic valve portion in a deployed configuration.

As shown in FIG. 5E, which illustrates the prosthetic valve portion 506 in a deployed or expanded configuration, the valve portion 506 can have a valve body 527 including an expandable/collapsible frame. The frame 527 can be similar to valve body or expandable/collapsible frame 427 shown in FIGS. 4A-4C. Further, similar to valve body 427, the prosthetic valve portion 506 can have a positioning member 536 configured as a ring and/or multiple elements or segments circumferentially coupled to a distal portion of and/or being integrally formed with the valve body 527 so that they can conform to the geometry of a native heart halve. It should be appreciated that the valve portion 506 can have any number of elements having any suitable configuration(s).

FIG. 5E shows that the anchor portion 510 can include distal, middle, and proximal portions 522, 524, 526. The distal and proximal portions 522, 526 of the anchor portion 510 can be configured to expand to form deployable wings 528, 530 shown in FIGS. 5C, 5D, and 5F. The deployed wings 528, 530 can be maintained in the expanded configuration until the anchor portion 510 is manipulated to cause the wings 528, 530 to collapse to the undeployed configuration. It should be appreciated that the implant 502 can include any other components not shown herein that are configured such that the anchor portion 510 can reversibly form the wings 528, 530.

Figure 5F:
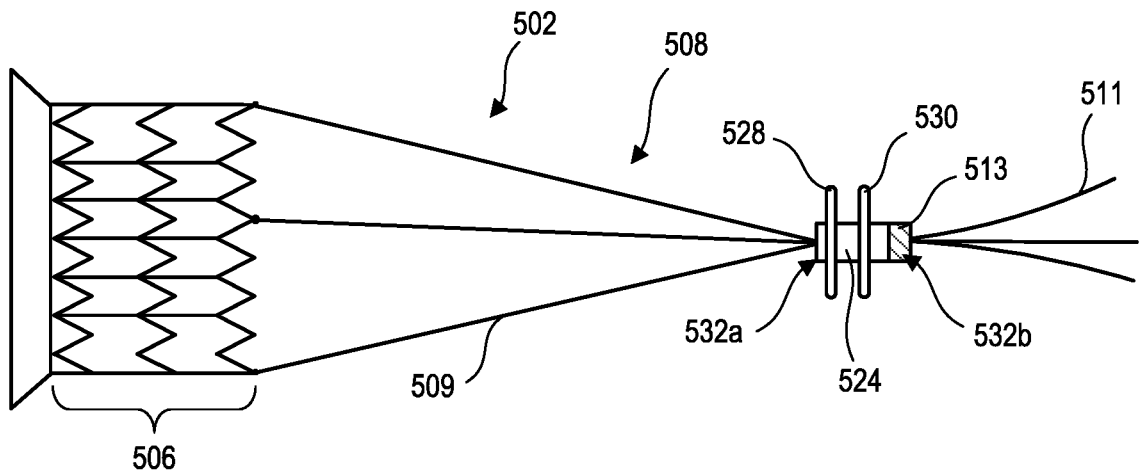
FIG. 5F is a side view of the implant of FIG. 5E showing the proximal and distal wings deployed.

As shown in FIGS. 5C-5F by way of a non-limiting example, the tether portion 508 can include one or more tethers 509 extending between the prosthetic valve portion 506 and the anchor portion 510. The tethers 509 can extend between the prosthetic valve portion 506 and the anchor portion 510 so that they also extend through the anchor portion 510 and protrude beyond the proximal end 532b of the anchor portion 510. FIGS. 5D and 5F illustrate proximal ends 511 of the tethers 509 extending from the proximal end 532b of the anchor portion 510.

As shown in FIG. 5E, the tethers 509 can be coupled to the prosthetic valve portion 506 at respective attachment points 516A, 516B, 516C, which can be done in any suitable manner. For example, the tethers 509 can be passed through one or more openings or apertures formed in the structural elements of the valve portion 506. In one exemplary embodiment, the tethers 509 can be integrally formed with the valve portion 506. Additionally or alternatively, the valve portion 506 can clamp the tether 509, and/or any retaining feature can be used to attach the tethers 509 to the prosthetic valve portion 506. It should be appreciated that three tethers 509 are shown in FIGS. 5C-5F as an example only, as the tether portion 508 can include any number of tethers (e.g., one, two, four, or more) that can be attached to the prosthetic valve portion 506 in any suitable manner.

The tether portion 508 can be formed from one or more absorbable or non-absorbable sutures (or any combination thereof) extending between the prosthetic valve portion 506 and the anchor portion 510. Thus, the tethers 509 can be flexible and/or elastic so that they can be tensioned at the distance between the prosthetic valve portion 506 and the anchor portion 510 is adjusted. Furthermore, the flexible and/or elastic nature of the tethers 509 can provide flexibility in the position of the valve portion 506 as the heart contracts and relaxes, so that the valve portion 506 can mimic the function of a native heart valve.

The tethers 509 can be retained in the implant 502 in a number of ways. In the illustrated embodiment, as shown in FIGS. 5C-5F, the anchor portion 510 can be coupled to or can include at the proximal end 532b thereof a tether lock 513 configured to reversibly lock the tethers 509 therein. The tether lock 513 can be a clamp or any other device configured to reversibly retain the tethers 509 in a fixed position. Although not illustrated, in some embodiments, the implant 502 can include a tether lock that is recessed into a body of the anchor portion 510 so that the lock does not protrude into the pericardial space.

In use, after the implant 502 is delivered transapically to the heart through outer shaft 504 of the introducer assembly, the prosthetic valve portion 506 can move from the undeployed or collapsed configuration (e.g., shown in FIGS. 5C and 5D) to a deployed or expanded configuration (e.g., shown in FIGS. 5E and 5F). The prosthetic valve portion 506 can be seated within the opening of a valve (e.g., a mitral valve) such that the valve body 527 is suspended off the tip of the mitral valve. The proximal end 532b of the anchor portion 510 can be mated with an actuator 534 (FIG. 5E) which can be used to manipulate the anchor portion 510 to cause the deployable distal and proximal wings 528, 530 to expand, as shown in FIG. 5F, to thereby anchor the implant 502 within the apex of the heart.

In some embodiments, prior to or after deploying the wings 528, 530, a length of the tether portion 508 can be adjusted. The adjustment can be made at any time point following the placement of the implant 502. For example, the actuator 534 (FIG. 5E) or any other suitable instrument can be mated to the tether lock 513 at the proximal end 532b and used to adjust the length of the tethers 509 so that the distance between the prosthetic valve portion 506 and the anchor portion 510 is adjusted to ensure a proper position of the valve portion 506 within a natural valve. In this way, the position of the prosthetic valve portion 506 in an expanded configuration, as shown in FIGS. 5E and 5F, can be adjusted. Additionally, in some embodiments, the prosthetic valve portion 506 and/or other portion(s) of the implant 502 can be rotated to adjust the position of the prosthetic valve portion 506.

The length of the tether portion 508 can be adjusted in any suitable manner. For example, an actuator, which can be any suitable adjustment tool configured to mate with the proximal end of the anchor portion 510, can be used to release a locking mechanism of the tether lock 513. In this way, one or more of the tethers 509 can be released to increase the length of the tether portion 508, or retracted (e.g., by being pulled) proximally to decrease the length of the tether portion 508. All of the tethers 509 can be adjustable together or one or more of the tethers 509 can be manipulated and adjusted separately from the other tethers of the tether portion 508, for example, to adjust a position of the prosthetic valve portion 506 within a natural heart valve.

It should be appreciated that the locking mechanism of the tether lock 513 can be manipulated in any suitable manner to adjust the length of the tether portion 508. After a desirable adjustment is complete, the tether lock 513 can be manipulated to lock the tethers 509 at the fixed position.

After the adjustment is complete, the actuator 534 can be removed, as shown in FIG. 5F. It should be appreciated that any portion of the tethers 509 can extend beyond the anchor 510 as the proximal portion 510, and, in some cases, some or all of the tethers 509 may not protrude beyond the proximal end 532b of the anchor portion 510.

Figure 5G:
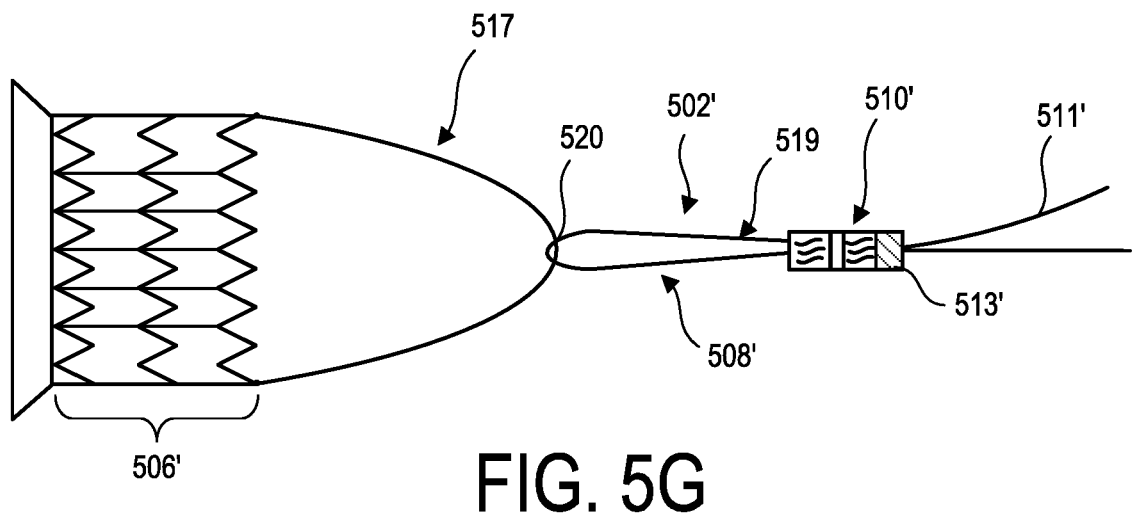
FIG. 5G is a side view of another implant in accordance with some embodiments.
Figure 5H:
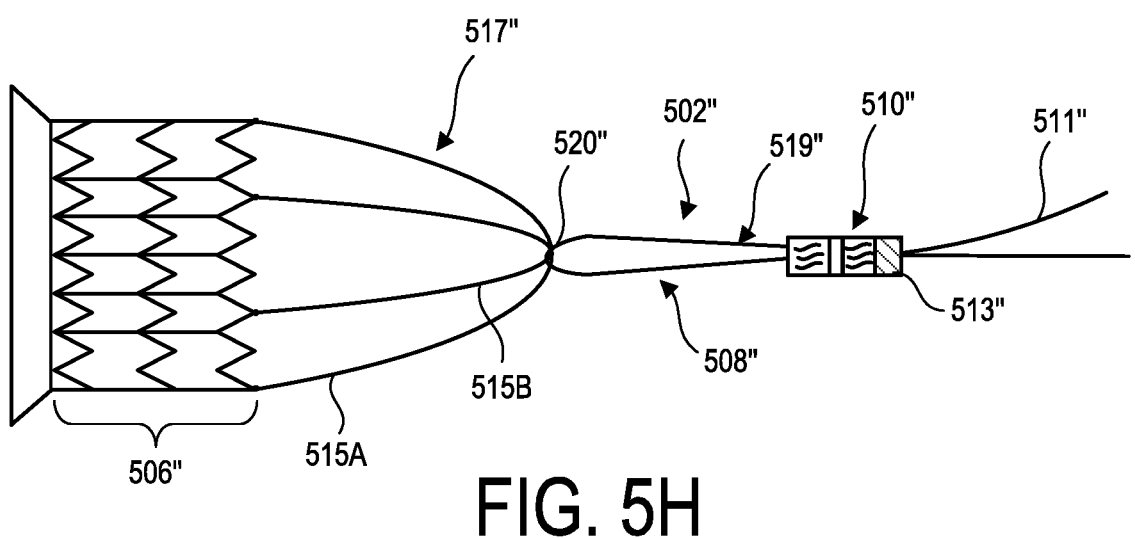
FIG. 5H is a side view of another implant in accordance with some embodiments.

FIGS. 5G and 5H illustrate other exemplary embodiments of an implant having an adjustable tether portion. In the exemplary embodiment of an implant 502' shown in FIG. 5G, a tether portion 508' has first and second portions 517, 519 formed from a flexible suture. The first, distal, portion 517 is attached to a prosthetic valve portion 506', whereas the second, proximal, portion 519 is slidably attached to an anchor portion 510'. As shown in FIG. 5G, the first and second portions 517, 519 can loop through each other at a junction 520. Proximal ends 511' of the tethers of the second portion 519 can extend through the anchor portion 510' and protrude beyond the proximal end thereof. Similar to the embodiment of FIGS. 5C-5F, the distance between the prosthetic valve portion 506' and the anchor portion 510' can be adjusted by manipulating a tether lock 513'.

In use, because the first and second portions 517, 519 can slide relative to each other at the junction 520, this loop arrangement of the portions 517, 519 allows the prosthetic valve portion 506' to swivel in any direction without disturbing the orientation of the anchor portion 510' (e.g., after its proximal and distal wings are deployed).

In the exemplary embodiment of FIG. 5G, the first and second portions 517, 519 each form one loop. One skilled in the art will appreciate that any number of loops can be included in the first and second portions of the tether portion. For example, FIG. 5H shows an implant 502" having a tether portion 508" which is similar to the tether portion 508' of the implant 502' in FIG. 5G. A first portion 517"of the tether portion 508" includes two loops 515A, 515B. As shown in FIG. 5H, the first portion 517" is coupled to a second portion 519" of the tether portion 508" at a junction 520". Similar to the embodiment of FIG. 5G, proximal ends 511" of the tethers of the second portion 519" can extend through the anchor portion 510" and protrude beyond the proximal end thereof. The distance between the prosthetic valve portion 506" and the anchor portion 510" can be adjusted by manipulating a tether lock 513" to adjust the length of the tether portion 508".

It should be appreciated that the implants in the embodiments described in connection with FIGS. 5C-5H can include any other components that can additionally or alternatively be used to adjust a position of a prosthetic valve within a natural heart valve. For example, in some embodiments, the tether portion of the implant can be used to manipulate the tethers to rotate the prosthetic valve or otherwise adjust its position. Furthermore, the tether locks 513, 513', 513" are shown by way of example only, as any other mechanism can be used to adjust the distance between the prosthetic and anchor portions.

Regardless of the particular configuration of an inner shaft and a tether portion that can extend between a prosthetic valve portion and an anchor portion, an actuator tool (e.g., the tool 134, 442, 534, or other suitable instrument) can be used to manipulate an implant (e.g., the implant 402, 502, 502', or 502") such that a distance between the prosthetic valve portion and the anchor portion is adjusted. Additionally or alternatively, the actuator or other suitable instrument can be used to rotate the entire implant or a portion thereof (e.g., the prosthetic valve portion). The actuator or other device that can be coupled to the anchor portion can be inserted percutaneously. Fluoroscopy or other suitable technique can be used to guide the adjustment process.

FIGS. 6A to 6J illustrate a method for repairing a heart valve of a patient using the exemplary system 100 described above in connection with FIGS. 1-3. Cross-sectional views of a patient's heart 602 are shown in FIGS. 6A-6J.

Figure 6A:
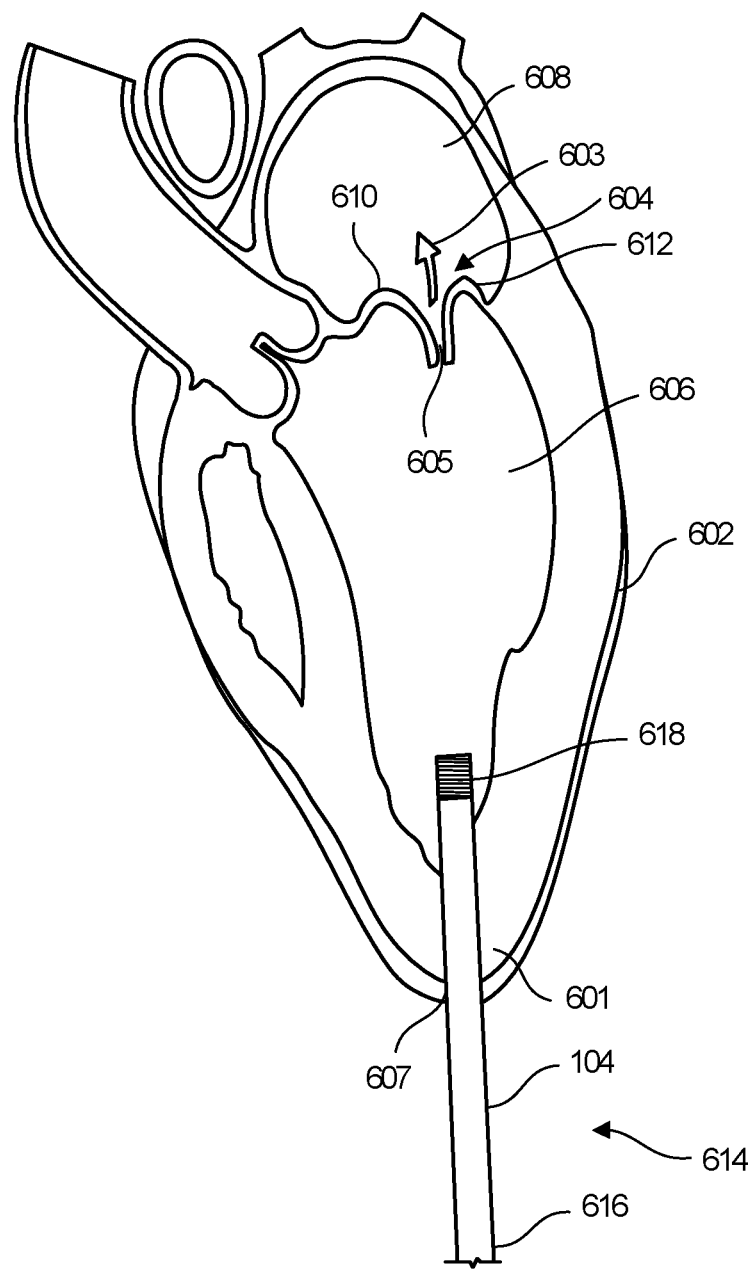
FIG. 6A is a cross-sectional view of a heart illustrating a method of delivering and deploying an implant in accordance with some embodiments.

FIG. 6A illustrates a cross-sectional view of a heart having a mitral valve 604 positioned between a left ventricle 606 and a left atrium 608. The mitral valve 604, which includes leaflets 610, 612, may become diseased such that it does not close properly when the heart 602 pumps out blood. In such condition, when the left ventricle 606 contracts, the blood leaks back (regurgitates) from the left ventricle 606, through the mitral valve 604, into the left atrium 608 in a direction shown by an arrow 603 in FIG. 6A. The mitral valve 604 can also have other defects which can be mitigated using the techniques described herein.

The system 100, which may be used to repair the regurgitated mitral valve 604, can include an introducer assembly 614 having an outer shaft 104 (also shown in FIG. 1A) having proximal and distal ends 616, 618. As shown in FIG. 6A, the outer shaft 104 (a portion of which is shown in FIG. 6A) may be introduced into the left ventricle 606 through an apex 601 of the heart 602 at an implantation site 607. The introducer assembly 614 can be manipulated to insert and advance the outer shaft 104 towards the left atrium 608 using, for example, a catheter system, or any other system.

Figure 6B:
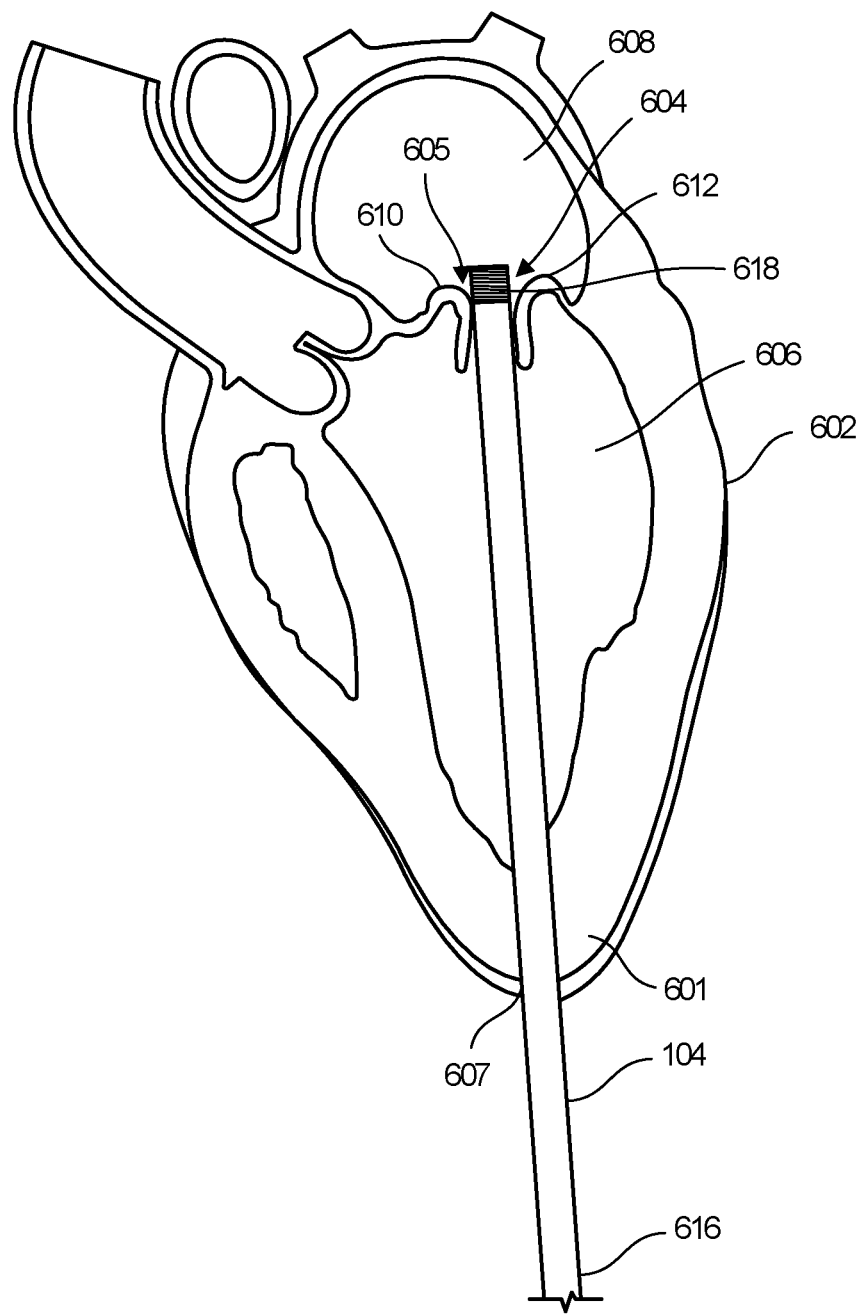
FIG. 6B is another cross-sectional view of a heart illustrating a method of delivering and deploying an implant in accordance with some embodiments.

The outer shaft 104, introduced through the apex 601, can be distally advanced further towards the left atrium 608. In this way, the shaft 104 can be manipulated to pass through an opening 605 of the mitral valve 604 until the distal end 618 of the outer shaft 104 is positioned within the left atrium 608, as shown in FIG. 6B. FIG. 6B illustrates that the distal end 618 can protrude above the opening 605 of the mitral valve 604. It should be appreciated that the outer shaft 104 can protrude into the left atrium 608 to any suitable distance, which allows the prosthetic valve to be deployed within the atrium.

In some embodiments, an implant can be delivered to the patient's heart through the outer shaft 104. The outer shaft 104 can have a lumen defined therein that can receive various components therethrough. The implant in accordance with some embodiments, such as the implant 102 in FIGS. 1-3, can be configured such that it can be removably inserted into the outer shaft 104 through its proximal end 616 and passed through the lumen of the outer shaft 104 towards the left atrium 608. The implant 102 can be passed through the outer shaft 104 such that its forward end 103 enters and exits the outer shaft 104 first. As shown in FIGS. 1A and 1B, the implant 102 can be configured such that it can be collapsed, or folded, and it can be inserted through the outer shaft 104 in this unexpanded configuration.

Figure 6C:
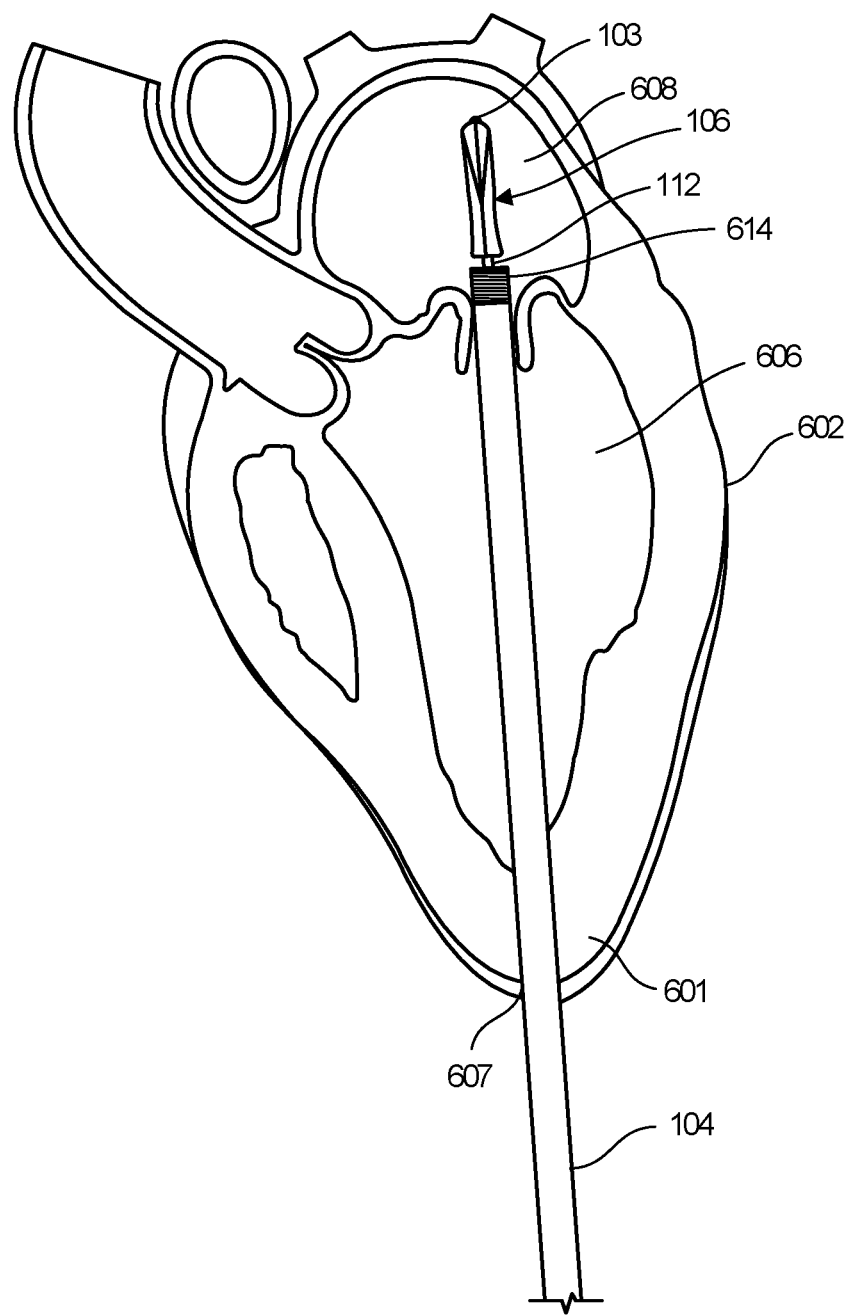
FIG. 6C is another cross-sectional view of a heart illustrating a method of delivering and deploying an implant in accordance with some embodiments.

Accordingly, as a result of advancing the implant 102 through the outer shaft 104, the prosthetic valve 106 located on the distal end of the implant 102 can be advanced in the undeployed configuration from the distal end 618 of the outer shaft 104 into the left atrial space, as shown in FIG. 6C. The prosthetic valve 106 can be coupled to the distal end 112 of the inner shaft 108 inserted through the outer shaft 104, a portion of which is shown protruding from the outer shaft 104 in FIG. 6C. In some embodiments, the prosthetic valve 106 can be integrally formed with the inner shaft 108.

Figure 6D:
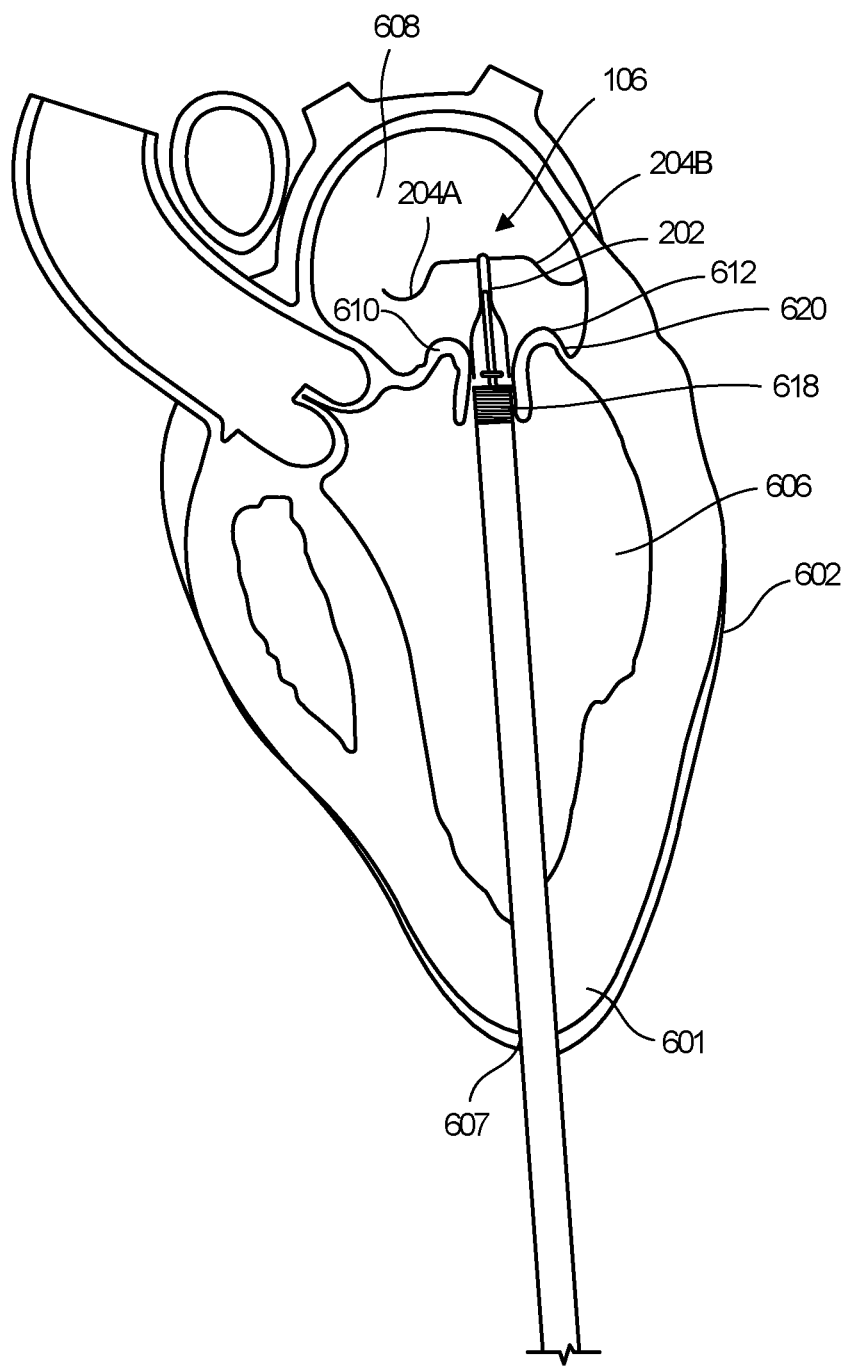
FIG. 6D is another cross-sectional view of a heart illustrating a method of delivering and deploying an implant in accordance with some embodiments.

As shown in FIG. 6D, the prosthetic valve 106 can be deployed such that it moves from the undeployed configuration to the deployed configuration and its valve body 202 and positioning members 204A, 204B (shown in FIGS. 2A, 2B and 3) are unfolded or expanded. Any suitable mechanism can be used to unfold the prosthetic valve 106. For example, the prosthetic valve 106 can operate like a spring-loaded umbrella that unfolds when actuated. However, other mechanisms can be used additionally or alternatively.

FIG. 6D illustrates that, prior to deployment of the prosthetic valve 106, the outer shaft 104 can be retracted from the left atrium 608 such that the distal end 618 thereof is positioned in the opening 605 of the mitral valve 604 between the leaflets 610 and 612. It should be appreciated that the described techniques are not limited to a specific position of the distal end 618 of the outer shaft 104, as the outer shaft 104 can be positioned differently depending on specifics of the patient's heart anatomy, the configuration of the prosthetic valve, and other factors.

Figure 6E:
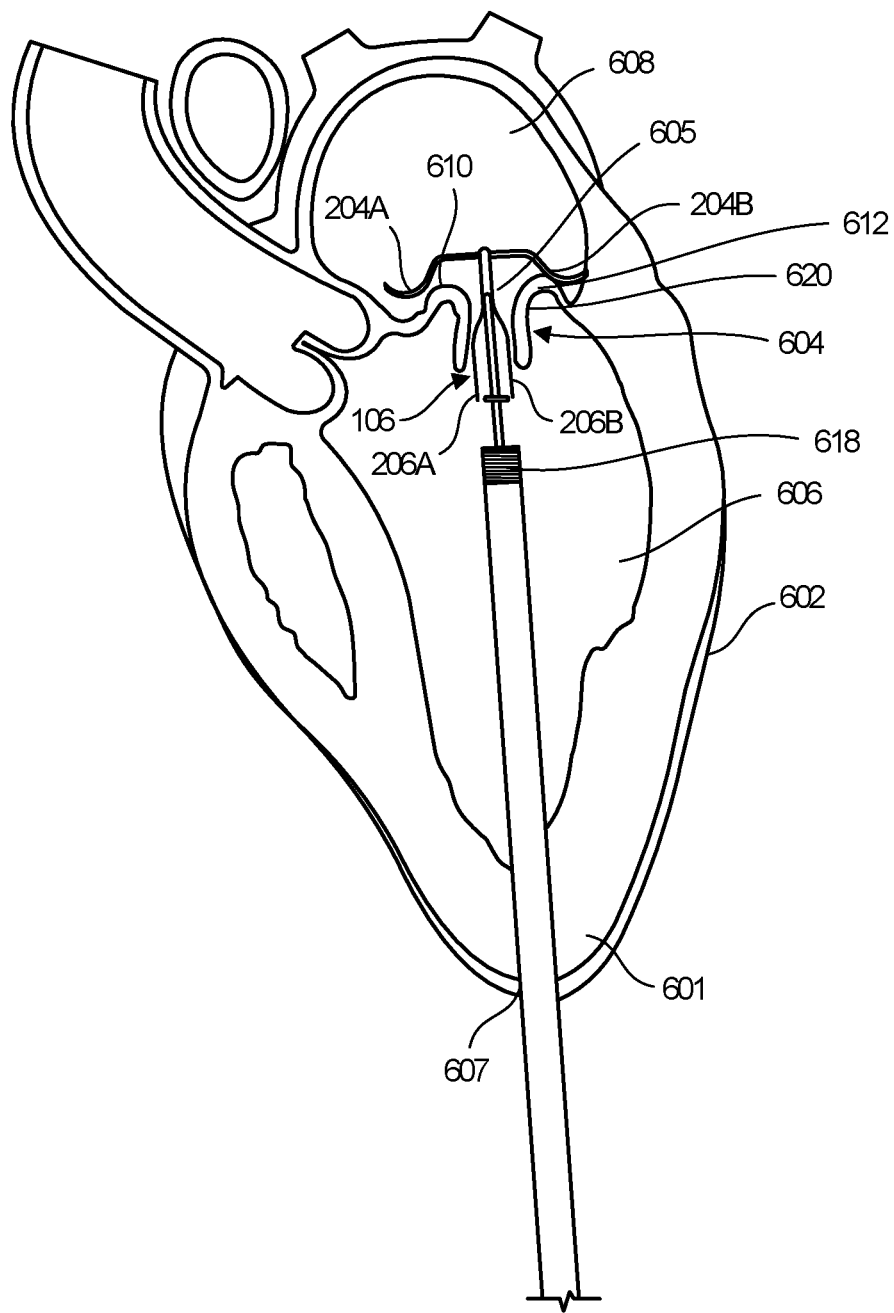
FIG. 6E is another cross-sectional view of a heart illustrating a method of delivering and deploying an implant in accordance with some embodiments.

FIG. 6D shows that the deployed prosthetic valve 106 can be initially positioned within the left atrium 608 such that its positioning members 204A, 204B are disposed within the left atrium 608 at a distance from the annulus 620 of the mitral valve 604. Next, the implant 102 can be manipulated such that the position of the prosthetic valve 106 with respect to the mitral valve 604 is adjusted to ensure proper positioning of the prosthetic valve 106. Thus, as shown in FIG. 6E, the outer shaft 104 carrying the implant 102 can be retracted from the left atrium 608 to the left ventricle 606. In this way, the prosthetic valve 106 can be moved proximally towards the mitral annulus 620 so that the positioning members 204A, 204B are disposed on opposite sides of the opening 605 of the mitral valve 604 and the valve body 202 is suspended within the opening 605. FIG. 6E shows that the leaflets 206A, 206B of the prosthetic valve 106 are positioned within the opening 605 of the mitral valve 604 between the native leaflets 610, 612.

The positioning members 204A, 204B can engage tissue of the mitral annulus 620 without penetrating therethrough. For example, the positioning members 204A, 204B, which may be at least partially flexible, can have a shape that allows them to frictionally engage the tissue of the mitral annulus. The positioning members 204A, 204B can thereby engage the tissue of the mitral annulus such that the valve body 202 is seated within the opening of the mitral valve 604. The positioning members 204A, 204B can be configured to engage tissue such that they resist dislodgment forces from the cardiac muscles and do not cause excessive disturbance to the tissue of the mitral annulus. As another advantageous characteristic of the described techniques, the prosthetic valve can be configured and deployed such that a risk of a left ventricular outflow tract (LVOT) obstruction can be reduced or eliminated, and the left ventricular (LV) function can be preserved. Accordingly, the risk of clotting can be reduced or eliminated.

In some embodiments, the location of the prosthetic valve 106 can be determined using suitable markers, such as, for example, one or more of the radiopaque markers 210A, 210B, 212A, 212B, and 213 shown in FIG. 3. The markers can be tracked using a suitable imaging technique and can thus be used to guide a surgeon when the implant 102 is delivered, deployed, adjusted, and/or removed.

Figure 6F:
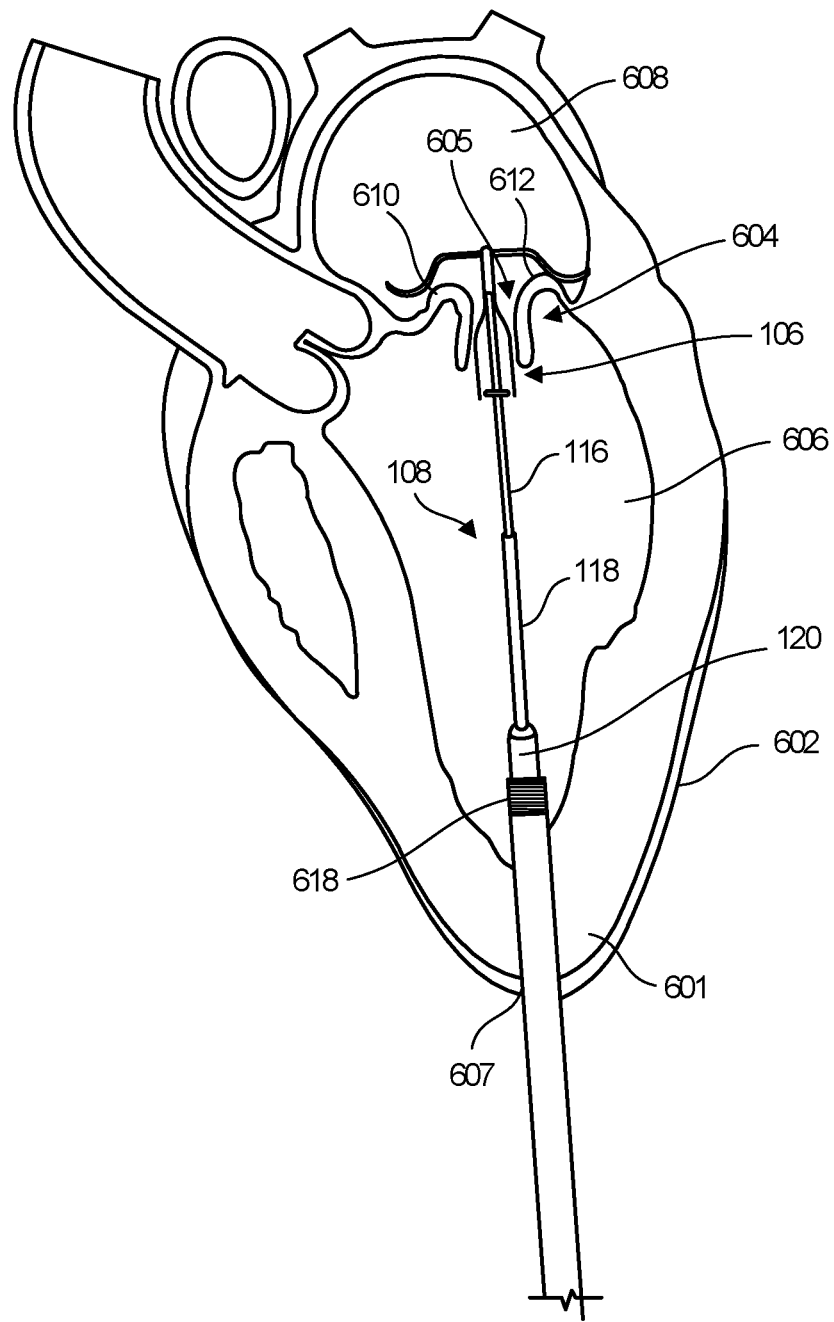
FIG. 6F is another cross-sectional view of a heart illustrating a method of delivering and deploying an implant in accordance with some embodiments.
Figure 6G:
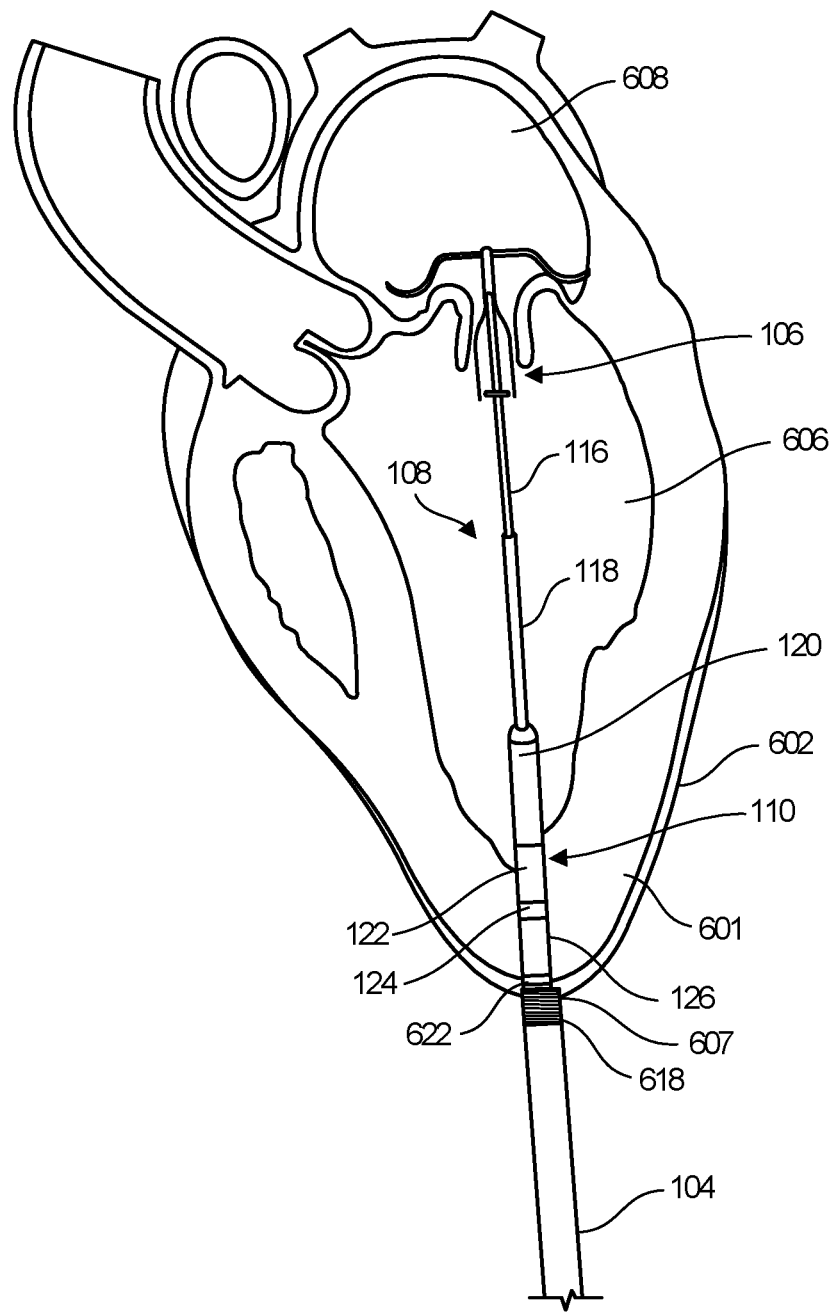
FIG. 6G is another cross-sectional view of a heart illustrating a method of delivering and deploying an implant in accordance with some embodiments.

As shown in FIG. 6F, after the prosthetic valve 106 is suspended within the opening 605 of the mitral valve 604, the outer shaft 104 can be retracted proximally towards the apex 601 of the heart 602 such that a portion of the inner shaft 108 can be exposed within the left ventricle 606. As discussed above, the inner shaft 108 can include distal, middle, and proximal portions 116, 118, 120. As the outer shaft 104 is retracted further towards the apex 601 such that it is eventually completely retracted from the left ventricle 606, as shown in FIG. 6G, the anchor portion 110 of the implant 102 can also be exposed. As shown in FIG. 6G, the implant 102 can be delivered to the heart 602 such that the anchor portion 110 can be positioned within the apex 601. As also shown in FIG. 1B, the anchor portion 110 can include distal, middle, and proximal portions 122, 124, 126.

Figure 6H:
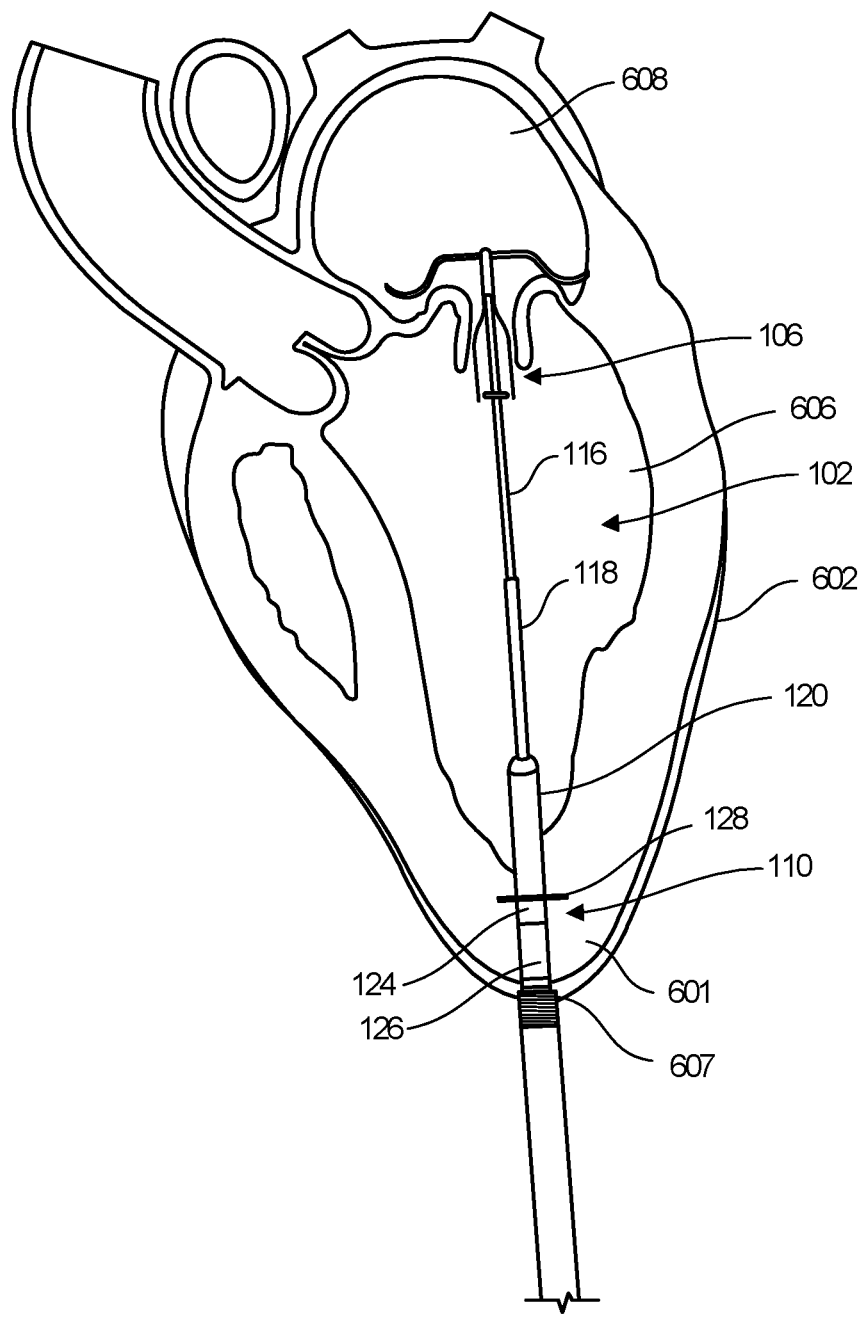
FIG. 6H is another cross-sectional view of a heart illustrating a method of delivering and deploying an implant in accordance with some embodiments.
Figure 6I:
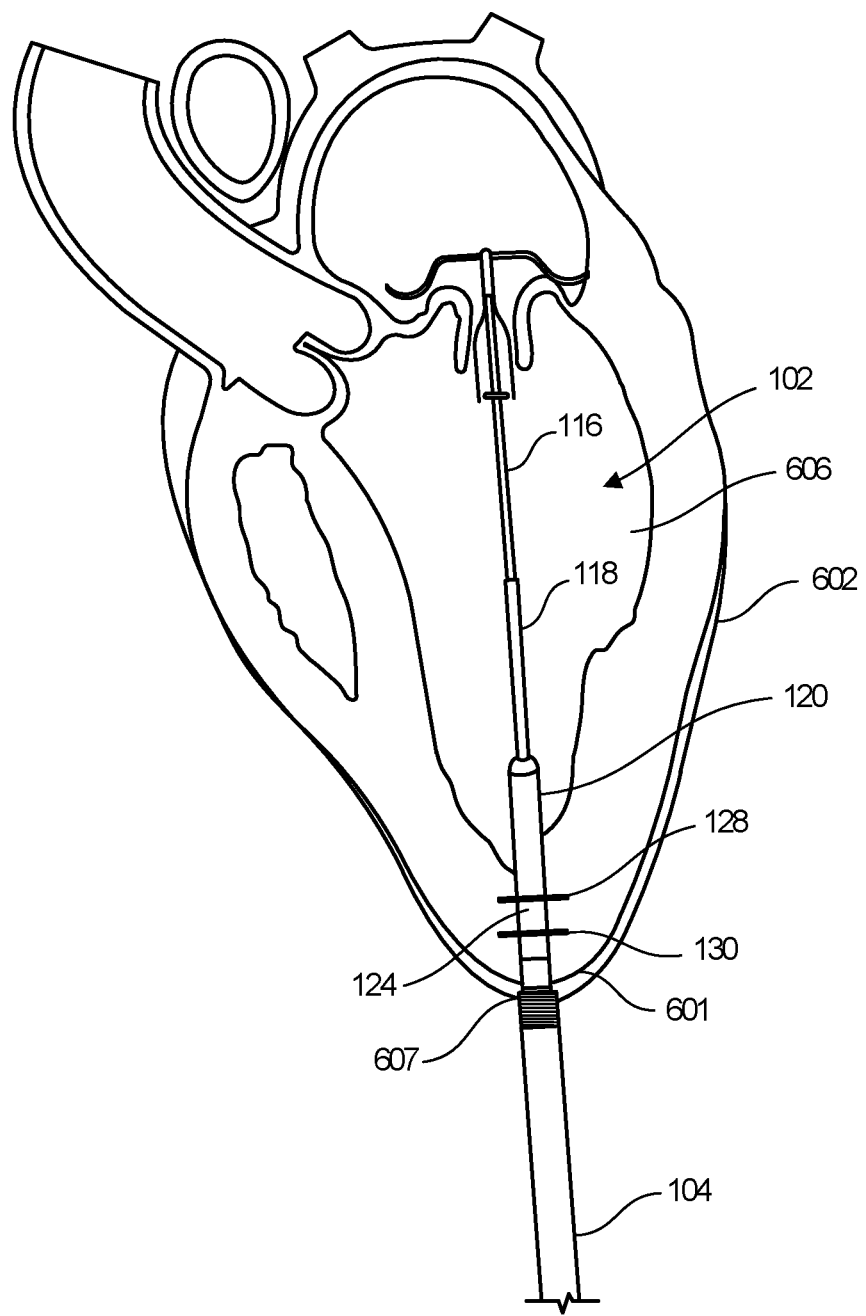
FIG. 6I is another cross-sectional view of a heart illustrating a method of delivering and deploying an implant in accordance with some embodiments.

As shown in FIG. 6G, a proximal end 622 of the anchor 110 is coupled (e.g., slidably or in other manner) to the distal end 618 of the outer shaft 104. The proximal end 622 is mated with an actuator, such as the actuator 442, (not shown), which can be used to manipulate the anchor 110 to cause it to deploy the deployable distal and proximal wings 128, 130 (FIGS. 1B and 2B) to thereby anchor the implant 102 within the apex of the heart. In this way, as shown in FIG. 6H, the distal portion 122 of the anchor 110 can first be expanded to form the distal wings 128. The proximal portion 126 of the anchor 110 can then be expanded to form the proximal wings 130, as shown in FIG. 6I. It should be appreciated that the distal wings 128 are shown to be deployed prior to deploying the proximal wings 130 by way of example only, and, in some embodiments, the proximal wings 130 can be deployed before the distal wings 128 are deployed. Also, in some embodiments, the distal and proximal wings 128, 130 can be deployed simultaneously or substantially simultaneously.

In some embodiments, prior to or after deploying the wings 128, 130, a length of the inner shaft 108 can be adjusted. The distal and middle portions 116, 118 of the inner shaft 108 can be configured to slide within each other. For example, the middle portion 118 can slide over the distal portion 116 to receive at least part of the distal portion 116 therein and reversibly lock in that configuration. In this way, the combined length of the middle and distal portions 116, 118 can be changed to thereby allow the length of the inner shaft 108 to be changed. Additionally, in some embodiments, the proximal portion 120 of the inner shaft 108 can be configured to receive a portion of the middle portion 118. After the length of the inner shaft 108 of the implant 102 is adjusted as desired, the implant 102 can be affixed within the apex of the heart.

The middle portion 124 of the anchor 110 can be positioned in tissue of the apex 601 and the wings 128, 130 can engage the tissue therebetween. The middle portion 124 can have a fixed length or, in some cases, the length of the middle portion 124 can be adjustable such that the middle portion 124 can traverse tissue walls having different thickness. FIG. 6I illustrates that the distal and proximal wings 128, 130 are positioned within tissue of the apex 601 of the heart 602. However, in some embodiments, the wings 128, 130 can be positioned at opposite sides of the apex wall, as the embodiments described herein are not limited to a specific way in which the deployable wings 128, 130 are positioned to anchor the implant 102 to the apex of the heart. In some embodiments, the distal wings 128 can be deployed against the wall of the apex of the heart and the proximal wings 130 can be deployed within the tissue. In other embodiments, the proximal wings 130 can be deployed against the wall of the apex of the heart and the distal wings 128 can be deployed within the tissue. In both of the above cases, the distal wings 128 can be deployed before, after, or simultaneously with deploying the proximal wings 130, as the described techniques are not limited in this respect.

Figure 6J:
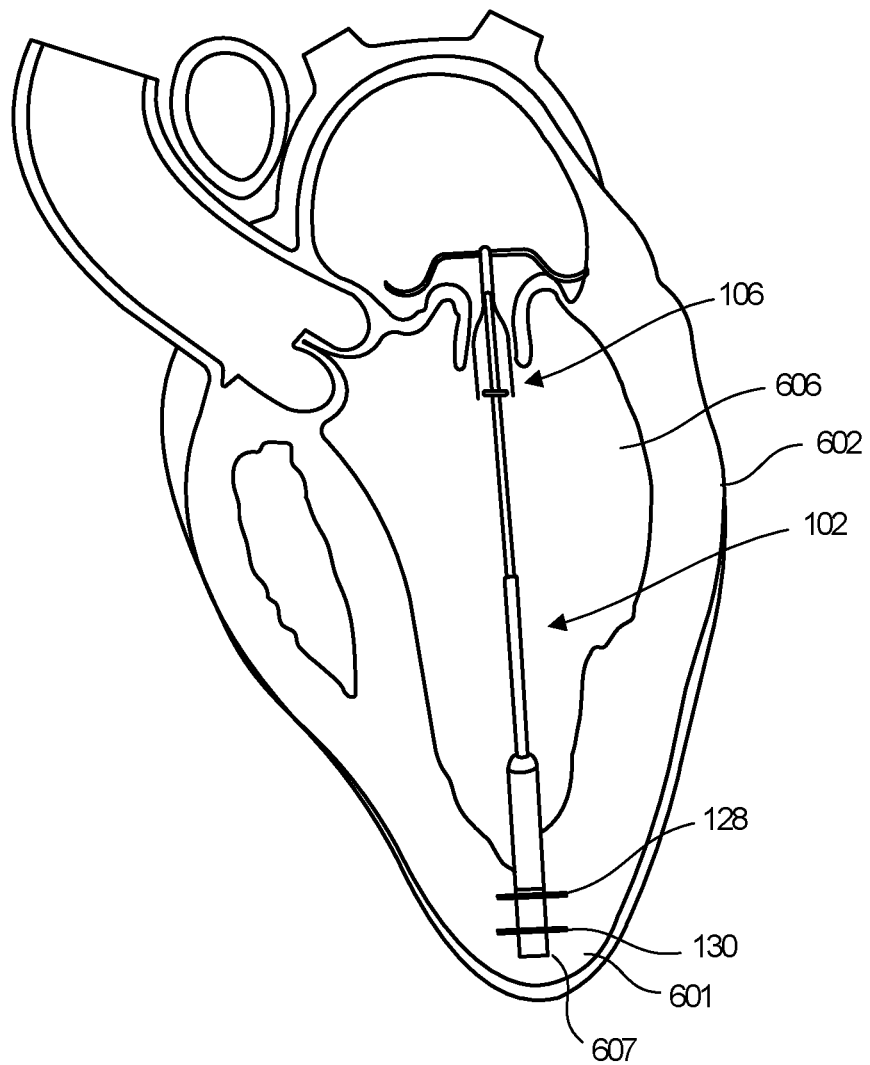
FIG. 6J is another cross-sectional view of a heart illustrating a method of delivering and deploying an implant in accordance with some embodiments.

Regardless of the manner and specific locations at which the distal and proximal wings 128, 130 are deployed, after the wings 128, 130 are deployed, the outer shaft 104 including suitable actuator tool(s) used to deploy the prosthetic valve 106 and the anchor 110 can then be removed from the implantation site such that the implant 102 having the prosthetic valve 106 suspended in the mitral valve is anchored within the apex of the heart, as shown in FIG. 6J.

Accordingly, the implant 102 can be removably deployed within the heart in a simple and cost-effective manner. The transapical delivery of the implant allows simplifying the surgical procedure and can lead to reducing trauma to the patient. An open heart surgery and the reliance on a cardiac bypass system can be avoided. The implant can be anchored in the apex of the heart without using sutures, purse strings or other additional attachment features. The site of the insertion of the implant can be closed in a clean manner, and a blood loss can be decreased.

In some embodiments, after the implant is anchored in the apex of the heart and the prosthetic valve is suspended off the annulus of a heart valve (e.g., a mitral valve), the distance between the prosthetic valve and the anchor can be adjusted. The anchor can be configured such that a proximal end thereof can receive a suitable adjustment tool which can then be used to adjust a length of the inner shaft to thereby adjust the position of the prosthetic valve within the mitral valve. In some embodiments, additionally or alternatively, the prosthetic valve only or the entire implant can be rotated while the implant is deployed.

In embodiments where one or more tethers can be used to couple the prosthetic valve portion to the anchor portion (e.g., as shown in FIGS. 5C-5H), a suitable adjustment tool can mate with the proximal end of the anchor portion and can be used to unlock the tether clamp to thereby adjust the position of the prosthetic valve within the heart valve (e.g., the mitral valve). When the adjustment is complete, the tether clamp can be manipulated to lock the tether to the anchor portion.

The implant can be adjusted to correct for a variety of conditions, and the adjustment can be made at any time point following the placement of the implant. For example, in cases when any part of the implant migrates from its position such that blood flows through a space between a structure of the implanted valve and cardiac tissue (e.g., a paravalvular leak occurs), the implant may need to be readjusted. The described techniques can allow treating the paravalvular leak or other conditions after the implant has been delivered into the heart. The implant can be adjusted (e.g., by adjusting the distance between the prosthetic valve and the anchor portion and/or rotating the implant or a portion thereof), or it can be completely removed which may be followed by a replacement of the prosthetic valve. Accordingly, the described techniques can provide a simplified and repeatable prosthetic valve implantation procedure which can reduce trauma to tissue and decrease risks associated with open heart surgery.

Figure 7A:
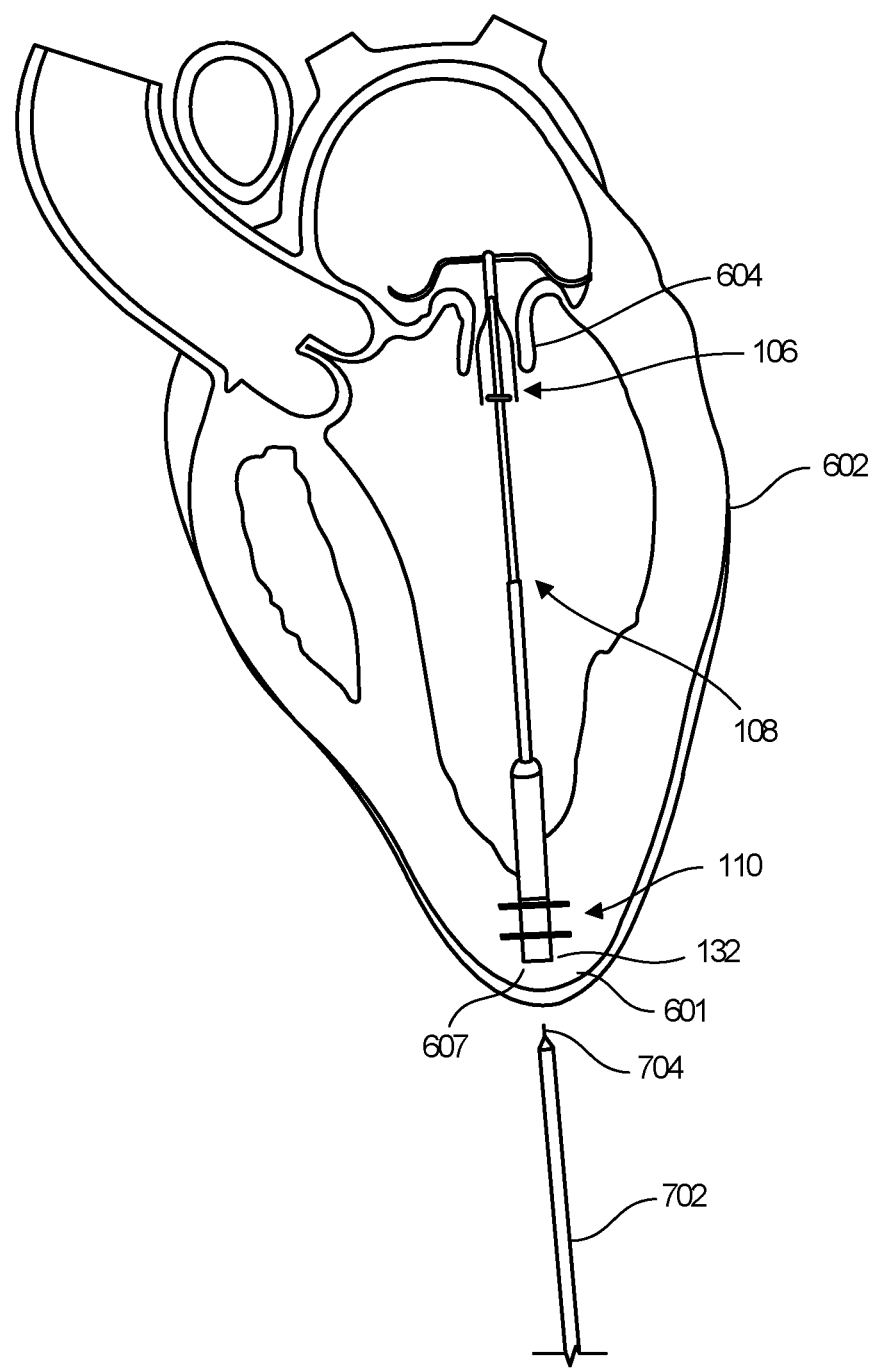
FIG. 7A is a cross-sectional view of a heart illustrating a method of adjusting the implant deployed as shown in FIGS. 6A-6J, in accordance with some embodiments.
Figure 7B:
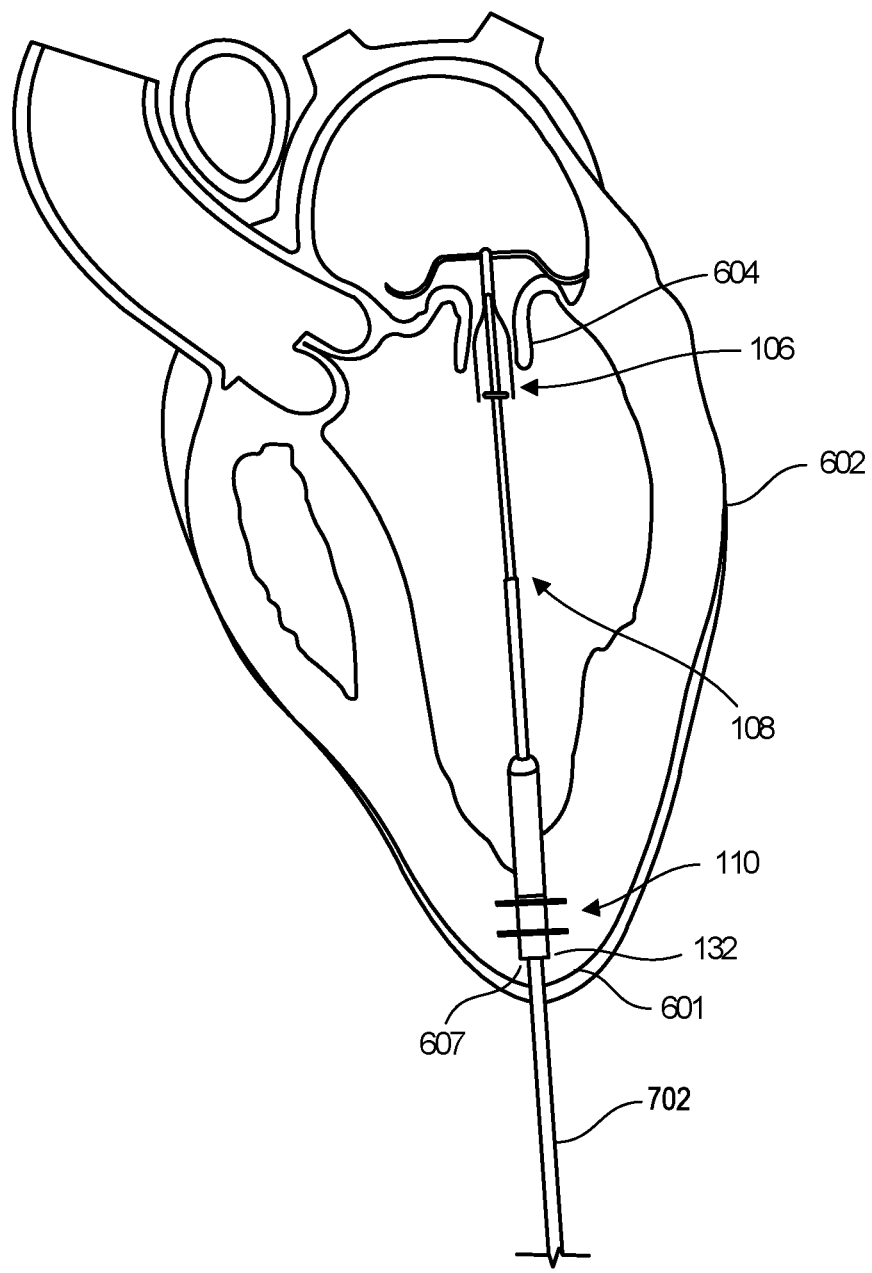
FIG. 7B is another cross-sectional view of a heart illustrating a method of adjusting the implant deployed as shown in FIGS. 6A-6J, in accordance with some embodiments.

FIGS. 7A and 7B illustrate that an adjustment tool 702 can be mated with the anchor 110 at the proximal end 132 of thereof. The adjustment tool 702 can be a screw driver or any other suitable tool. The screw driver can have a hollow shaft. A distal end of the adjustment tool 702 can be inserted into the anchor 110 and the adjustment tool 702 can be used to adjust the length of the inner shaft 108 to thereby raise or lower the prosthetic valve 106 relative to the mitral valve 604 to adjust a position of the implant during the movement of the mitral valve 604 upon beating of the heart.

In embodiments including a tether portion configured to adjust a distance between the prosthetic valve and anchor portions (e.g., embodiments shown in FIGS. 5C-5H), the adjustment tool 702 can be placed over one or more tethers extending beyond the proximal end of the anchor portion and the tool 702 can be used to manipulate a locking portion (e.g., the tether lock 513) configured to reversibly retain the tether(s). In this way, the distance between the prosthetic valve portion and the anchor portion can be adjusted.

As discussed above, the implant in accordance with some embodiments can be removed from the implantation site in a simple, time-efficient, and non-invasive manner. Following the removal, another implant can be inserted to the site of the deficient native valve, for example, when an implant needs to be positioned differently, a different type of an implant is desired, or for any other reasons. Accordingly, the implant placement procedure in accordance with some embodiments can be repeatable without causing trauma to the cardiac tissue.

Figure 8A:
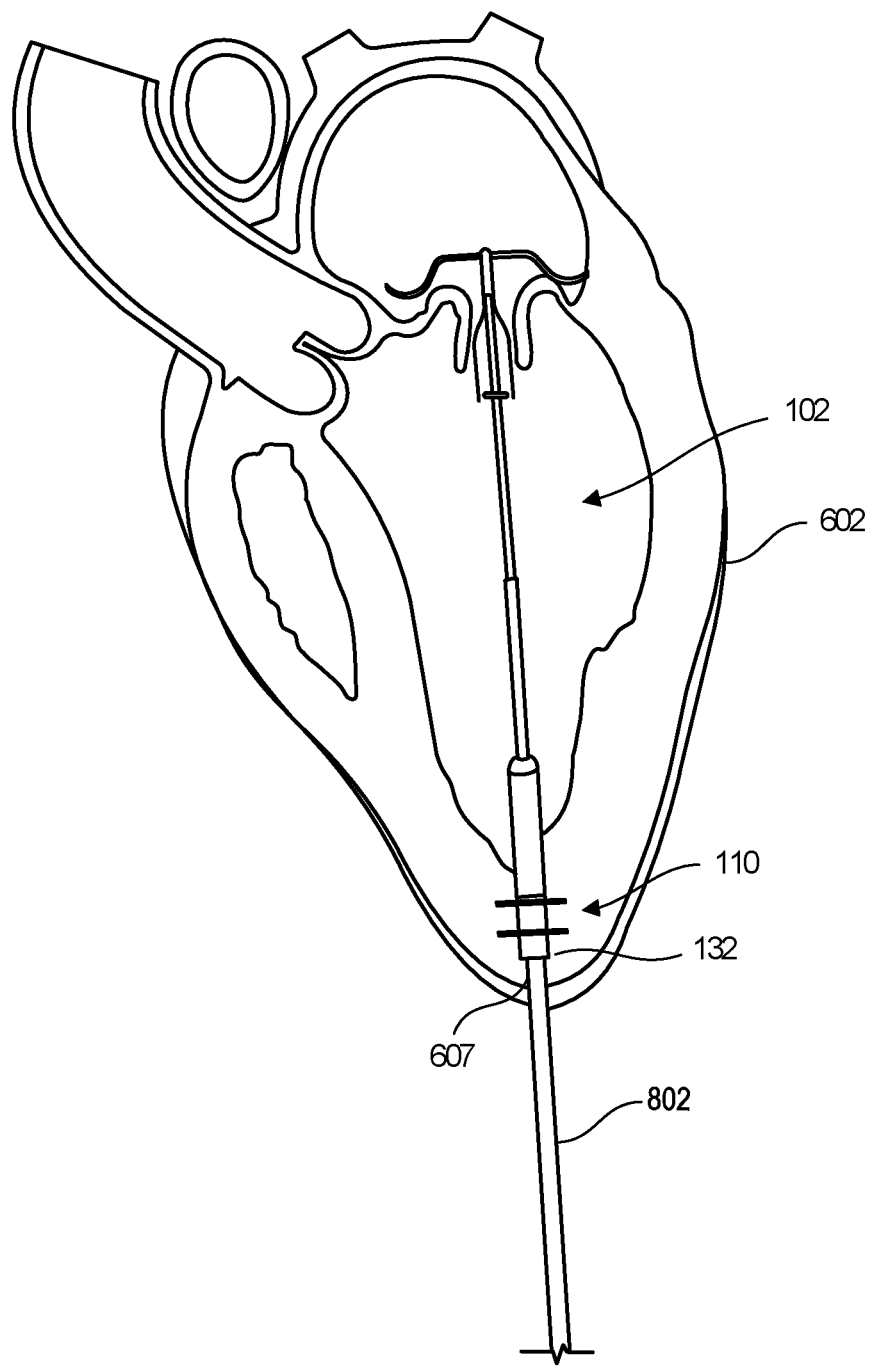
FIG. 8A is a cross-sectional view of a heart illustrating a method of removing the implant deployed as shown in FIGS. 6A-6J, in accordance with some embodiments.
Figure 8B:
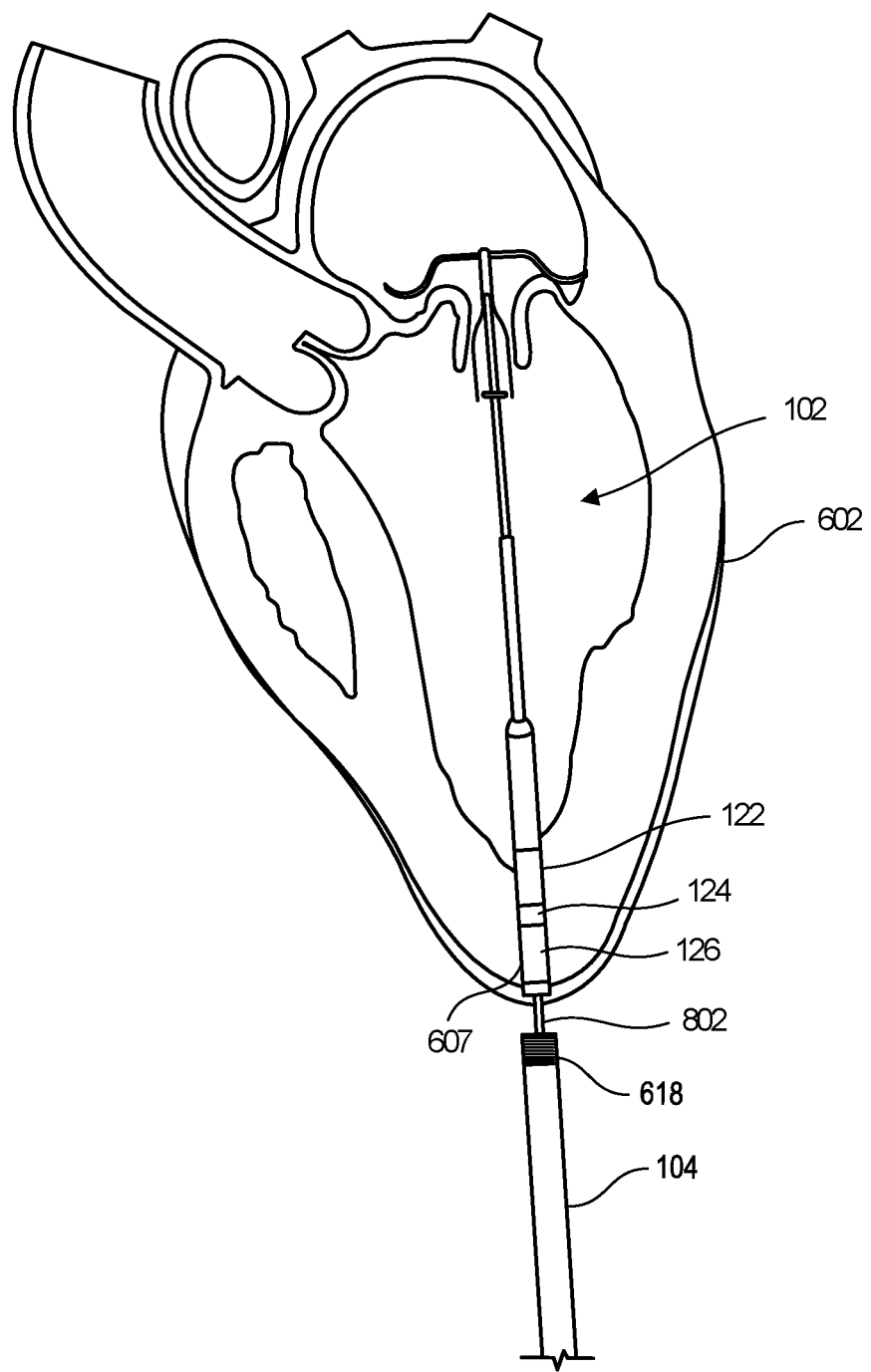
FIG. 8B is another cross-sectional view of a heart illustrating a method of removing the implant deployed as shown in FIGS. 6A-6J, in accordance with some embodiments.
Figure 8C:
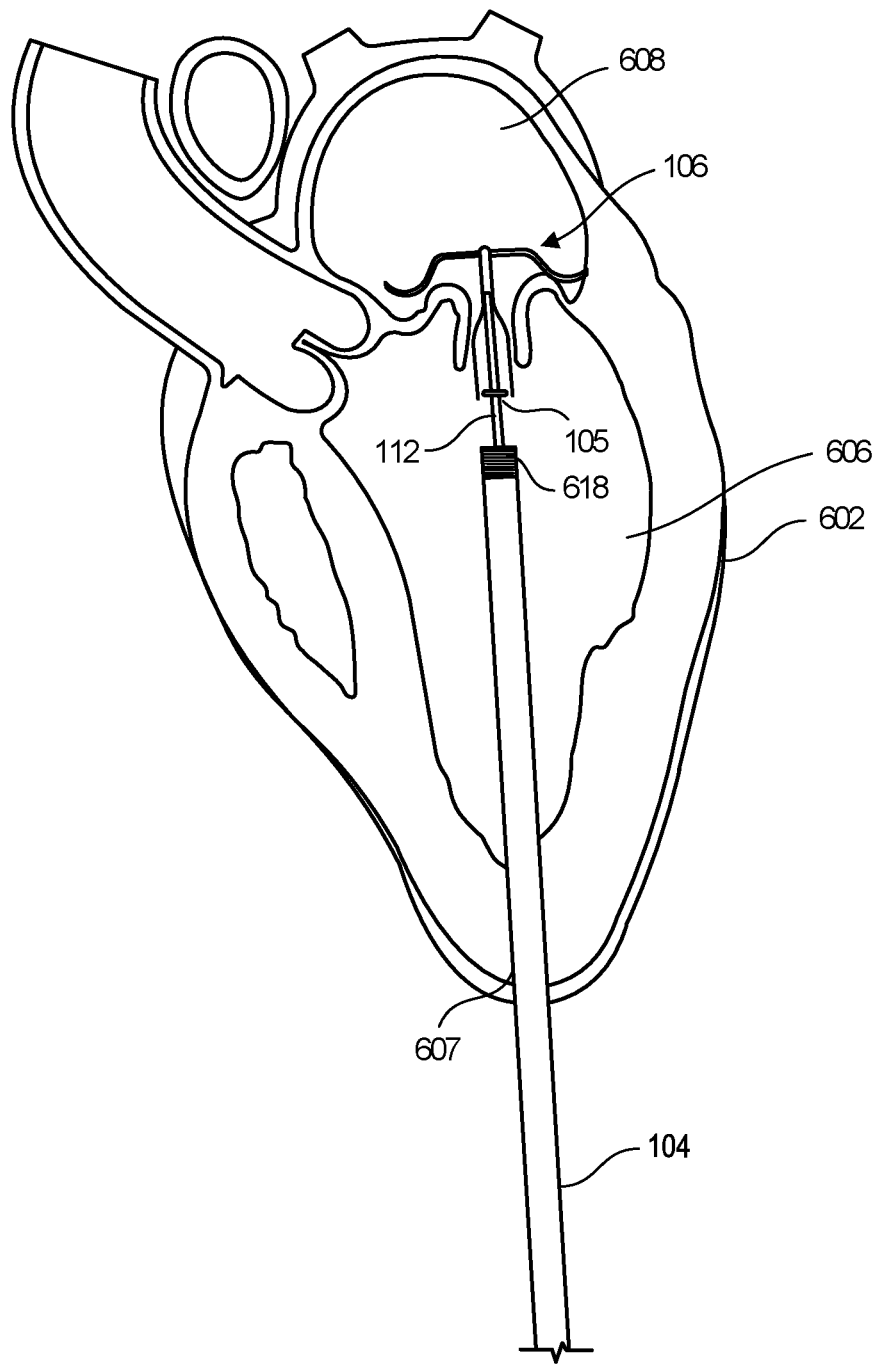
FIG. 8C is another cross-sectional view of a heart illustrating a method of removing the implant deployed as shown in FIGS. 6A-6J, in accordance with some embodiments.

FIGS. 8A to 8F illustrate a reverse process of removing the implant 102 delivered and deployed as shown in connection with FIGS. 6A-6J. FIG. 8A shows that a reversal tool 802, which can be any suitable instrument, can be mated with the proximal end 132 of the deployed implant 102. The tool 802 can be any suitable instrument and can be locked into position when inserted through the proximal end 132 to move the deployed wings 128, 130 from the expanded configuration to the unexpanded configuration. In FIG. 8B, the anchor 110 is shown with the wings 128, 130 collapsed, such that distal and proximal portions 122, 126 of the anchor 110 are shown in a pre-deployed configuration, without the wings formed. Next, as also shown in FIG. 8B, the outer shaft 104 can be inserted over the reversal tool 802 and advanced distally over the implant 102 having the wings 128, 130 collapsed, towards the left atrium 608. The outer shaft 104 can be advanced into the left ventricle 606 until the distal end 618 thereof is located in proximity to the proximal end 105 of the prosthetic valve 106, as shown in FIG. 8C. In some embodiments, as shown in this example, the outer shaft 104 can be advanced distally until only the distal end 112 of the inner shaft 108 is exposed.

Figure 8D:
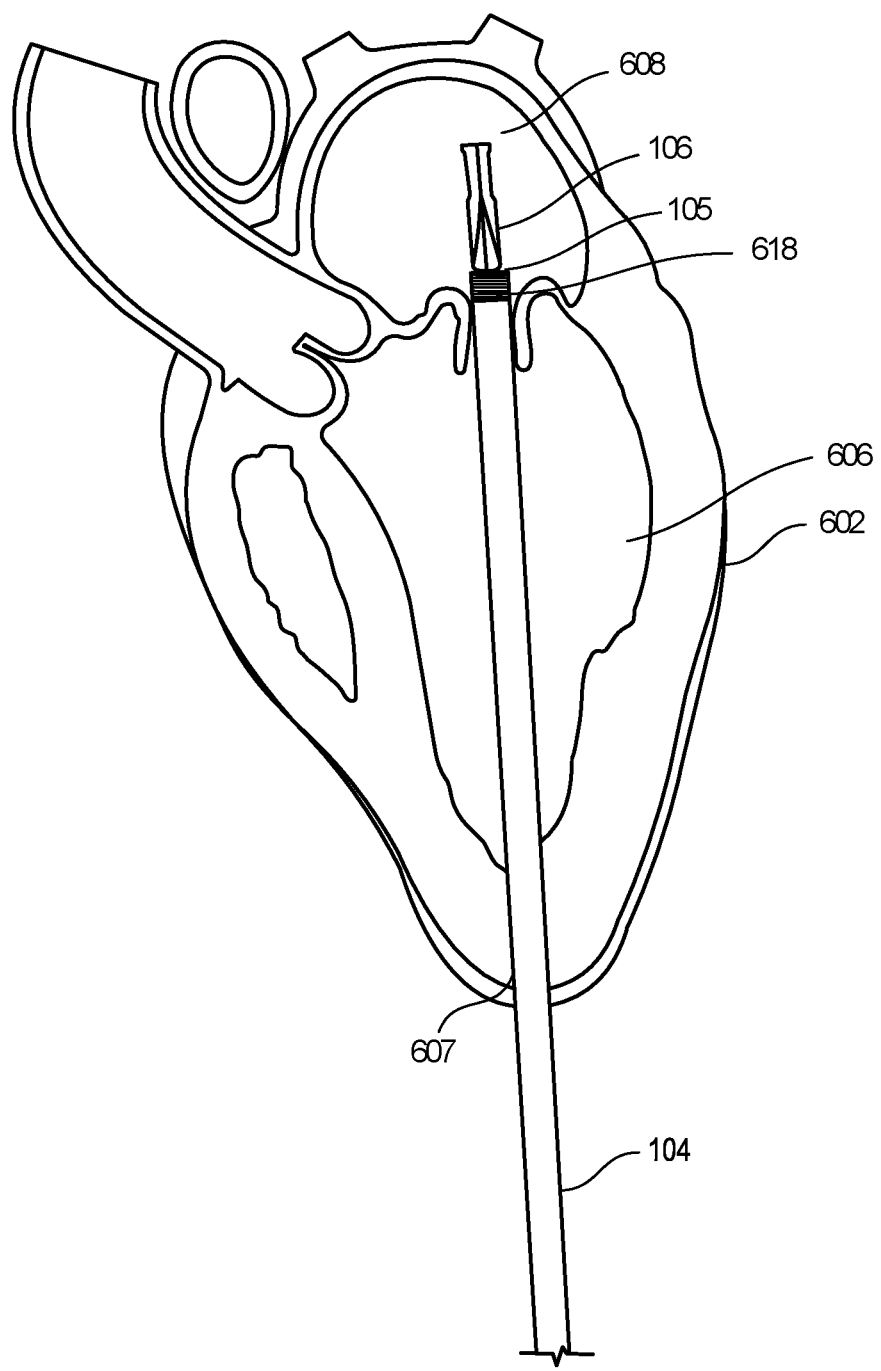
FIG. 8D is another cross-sectional view of a heart illustrating a method of removing the implant deployed as shown in FIGS. 6A-6J, in accordance with some embodiments.

FIG. 8D demonstrates that the outer shaft 104 can be inserted further such that its distal end 618 is positioned within the left atrium 608. The prosthetic valve 106 can then be collapsed in a suitable manner. For example, in one embodiment, the prosthetic valve portion 106 can be pulled proximally or otherwise manipulated which causes the positioning members 204A, 204B and leaflets 206A, 206A to collapse like a reverse umbrella. In this way, the prosthetic valve 106 can move from the expanded configuration to the unexpanded configuration in which the valve 106 is compressed and can fit into the outer shaft 104 for removal. It should be appreciated that the mechanism of collapsing the prosthetic valve 106 is shown by way of example only, as the prosthetic valve 106 can have any other structure which can allow the valve to expand/collapse in any suitable manner.

Figure 8E:
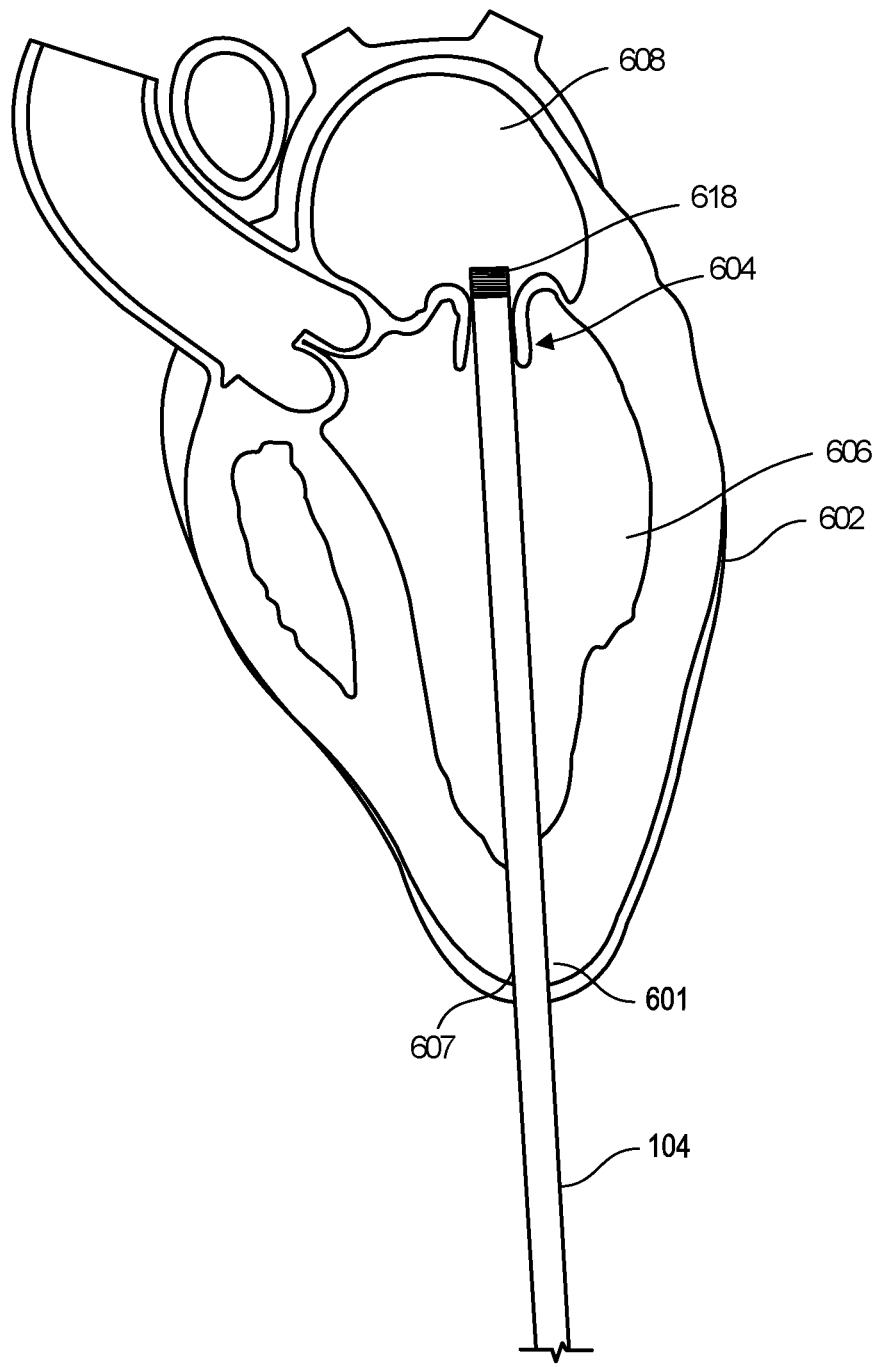
FIG. 8E is another cross-sectional view of a heart illustrating a method of removing the implant deployed as shown in FIGS. 6A-6J, in accordance with some embodiments.

After the prosthetic valve 106 is collapsed, the implant 102 can be removed from the implantation site through the outer shaft 104 (e.g., using the reversal tool 802 or other instrument). Thus, FIG. 8E shows a cross-section of the heart 602 where the prosthetic valve 106 has been pulled into the outer shaft 104 and only the outer shaft 104 is visible.

Figure 8F:
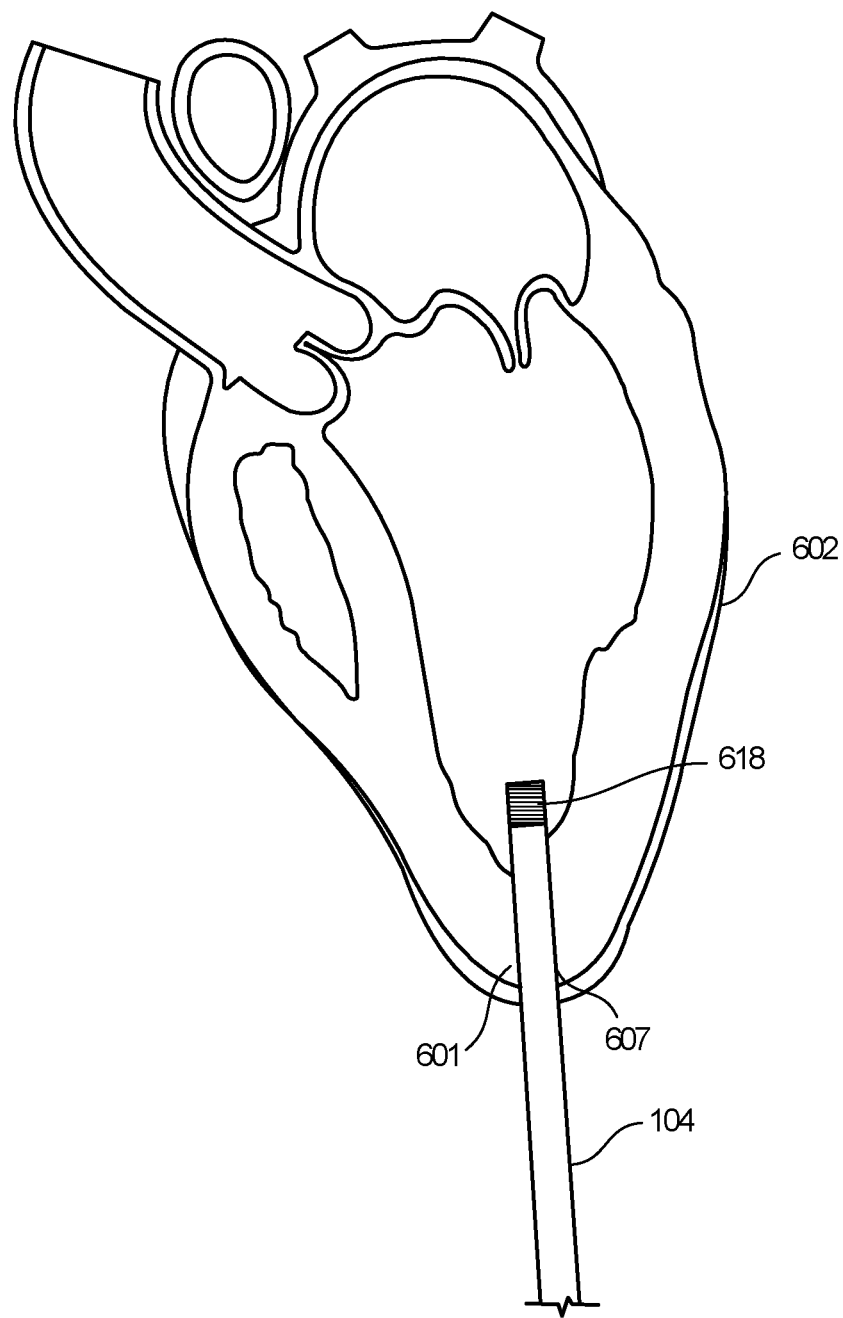
FIG. 8F is another cross-sectional view of a heart illustrating a method of removing the implant deployed as shown in FIGS. 6A-6J, in accordance with some embodiments.

After the implant 102 is removed from the left atrium 608 through the outer shaft 104, the outer shaft 104 can be moved further from the left atrium 608 through the mitral valve 604 into the left ventricle 606. While still being located within the left ventricle 606, the outer shaft 104 can be positioned such that its distal end 618 extends above the apex 601 of the heart 602, as shown in FIG. 8F. In some embodiments, the outer shaft 104 can be completely removed from the implantation site. Furthermore, in some embodiments, the site 607 of implantation of the implant 102 can then be closed, as shown in FIGS. 9A to 9E.

Figure 9A:
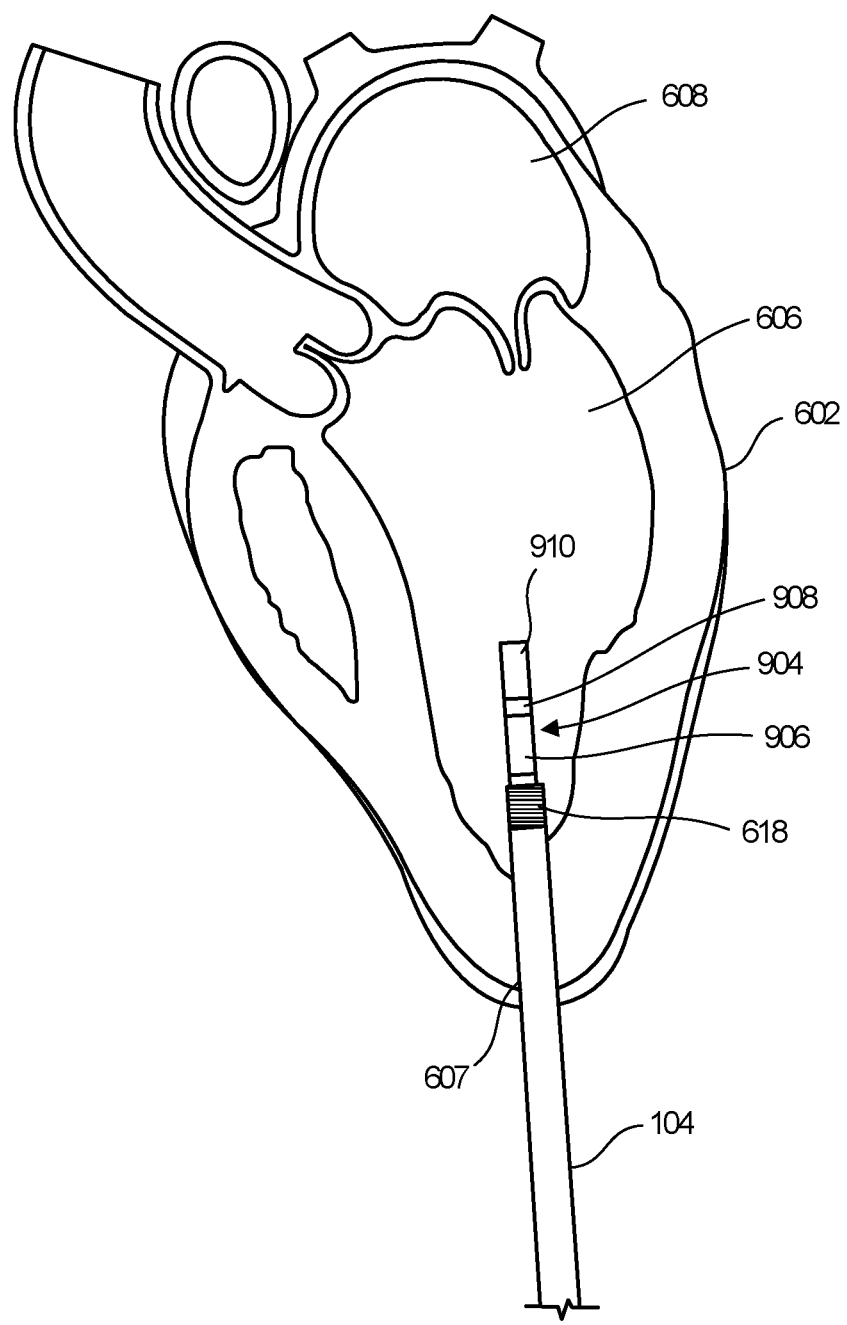
FIG. 9A is a cross-sectional view of a heart illustrating a method of sealing the site of implantation of the implant, in accordance with some embodiments.

FIG. 9A shows that an additional implant, referred to herein as a closure implant or closure device 904, can be introduced through the outer shaft 104, advanced distally through the lumen of the shaft 104, and released from the distal end 618 of the shaft 104. The closure device 904 can be configured similarly to the anchor portion 110 or in any other suitable manner.

Figure 9B:
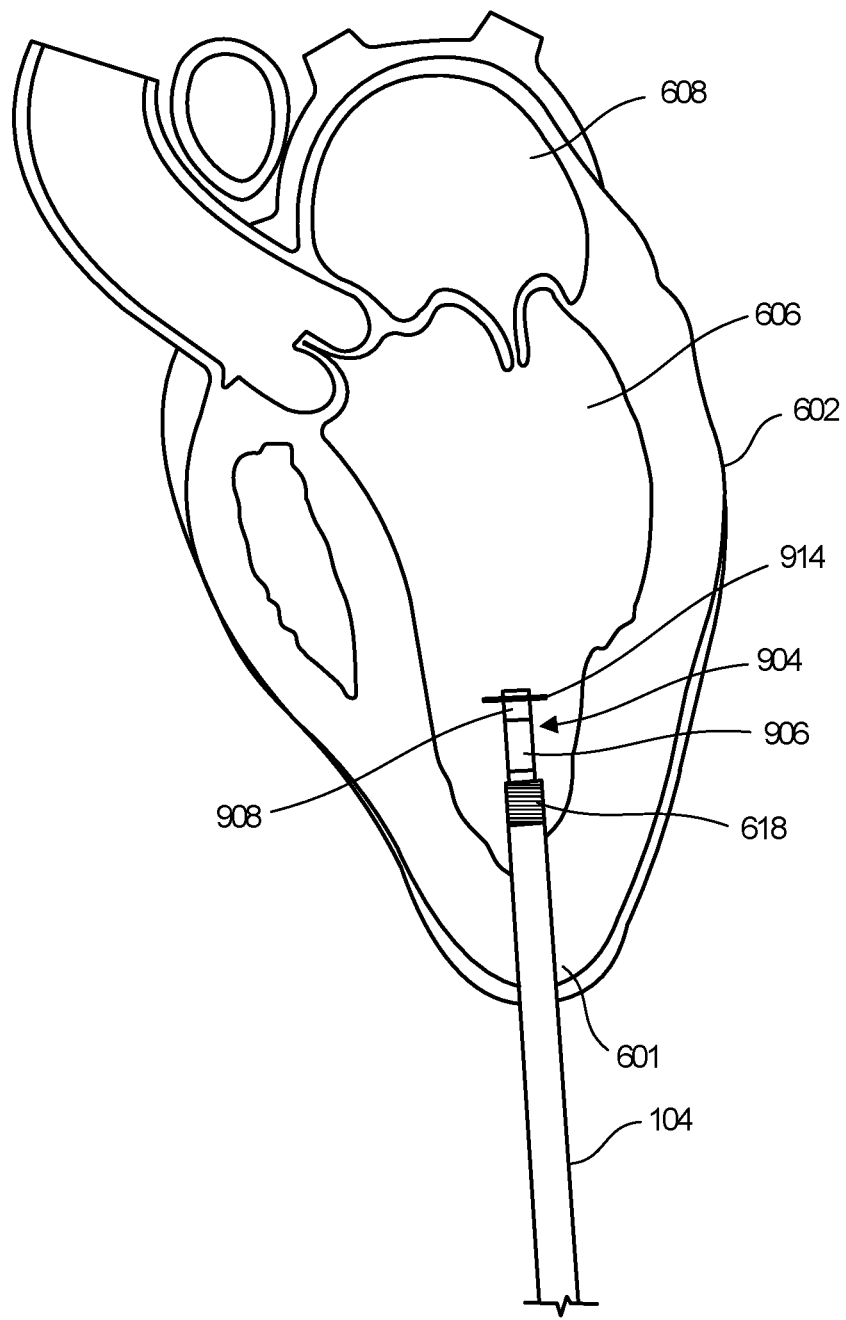
FIG. 9B is another cross-sectional view of the heart illustrating a method of sealing the site of implantation of the implant, in accordance with some embodiments.
Figure 9C:
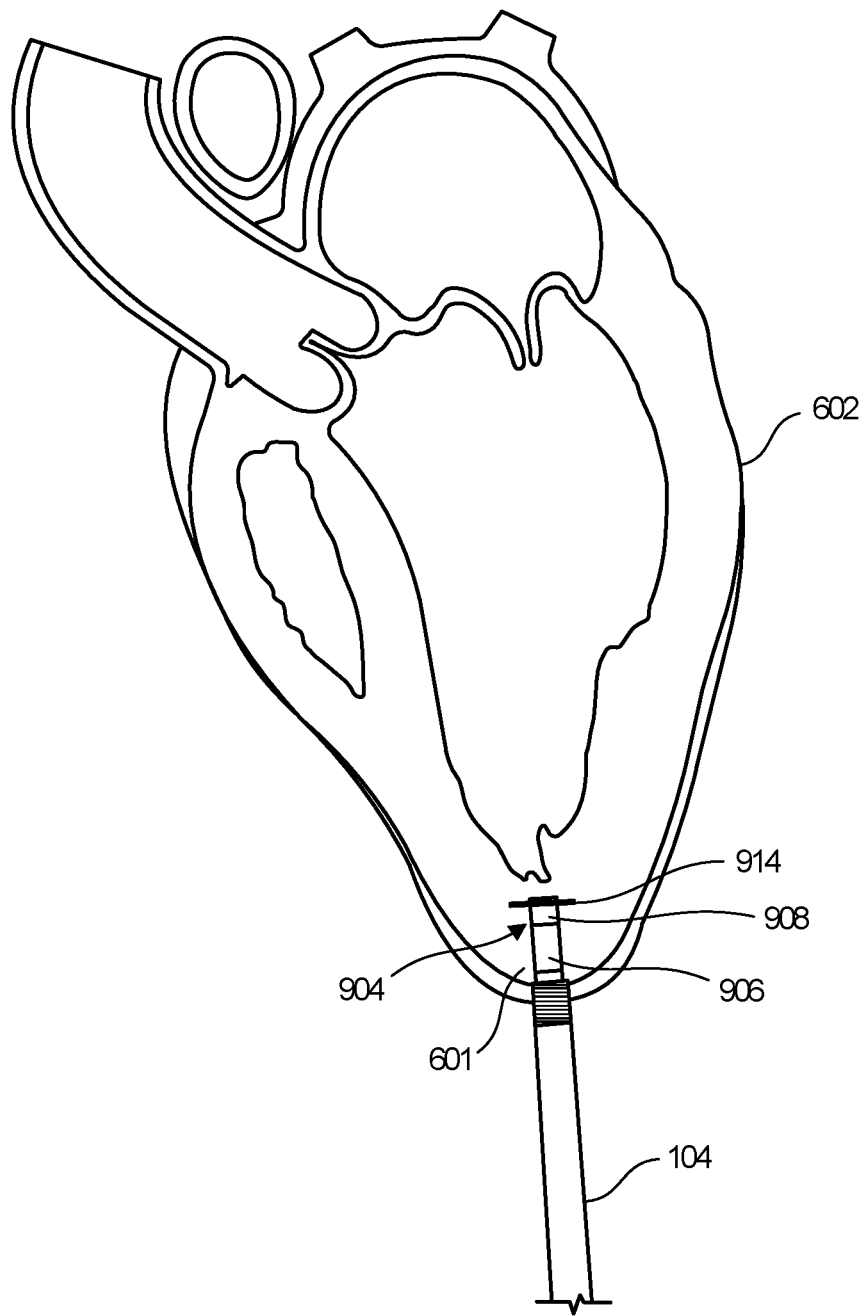
FIG. 9C is another cross-sectional view of the heart illustrating a method of sealing the site of implantation of the implant, in accordance with some embodiments.
Figure 9D:
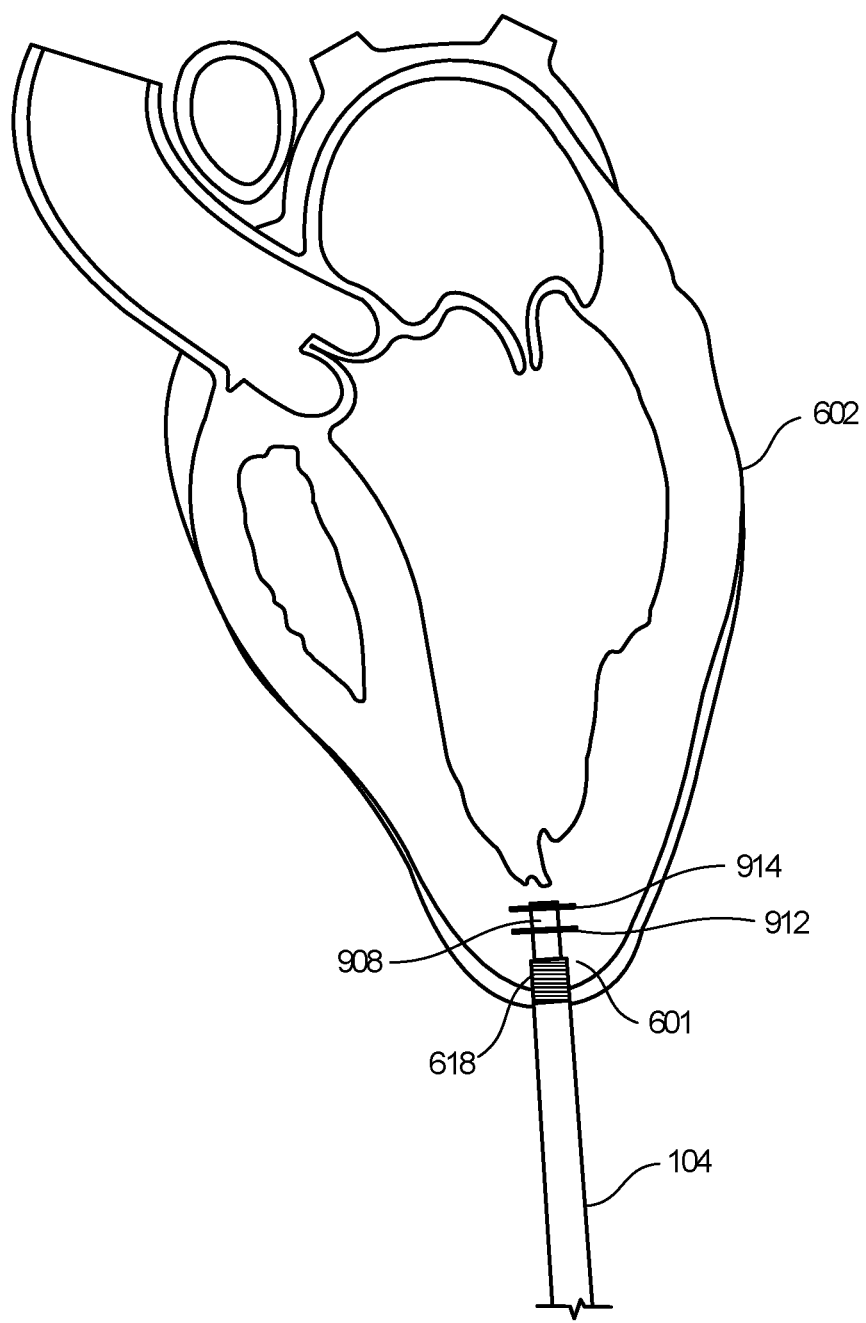
FIG. 9D is another cross-sectional view of the heart illustrating a method of sealing the site of implantation of the implant, in accordance with some embodiments.
Figure 9E:
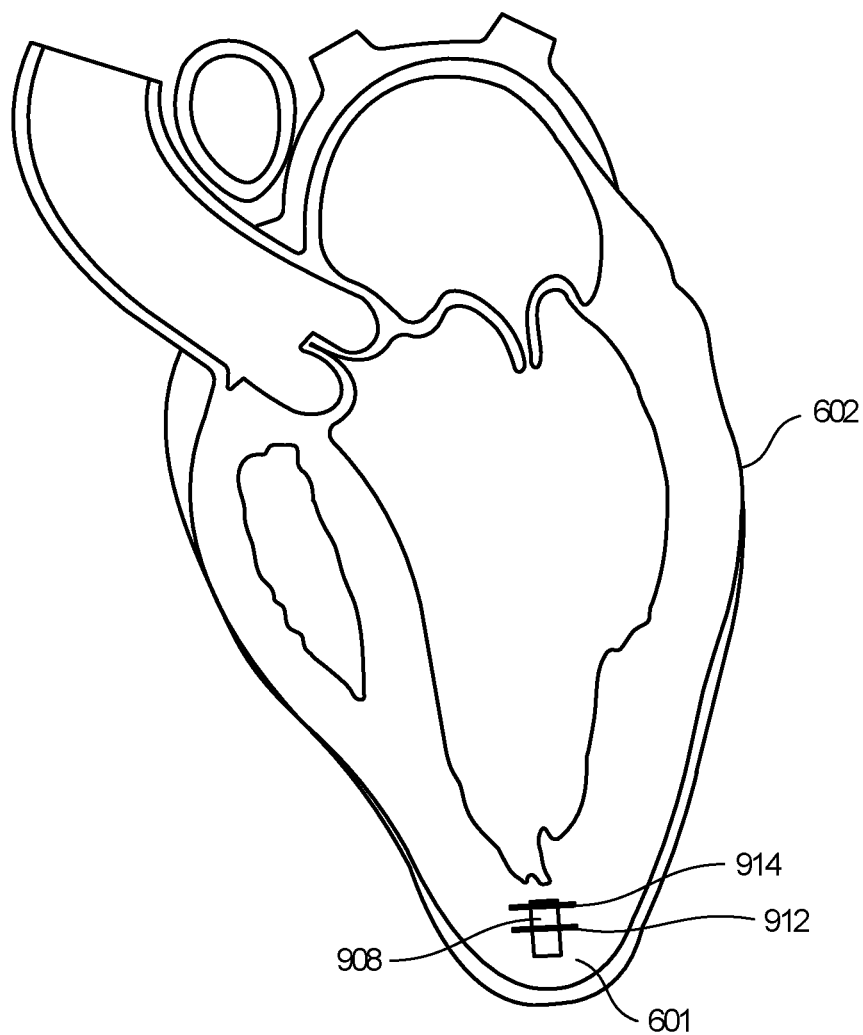
FIG. 9E is another cross-sectional view of the heart illustrating a method of sealing the site of implantation of the implant, in accordance with some embodiments.

In the embodiment of FIGS. 9A-9E, the closure implant 904 can include proximal, middle, and distal portions 906, 908, 910, and the proximal and distal portions 906, 910 can be configured to expand to form proximal and distal deployable wings 912, 914, both shown in FIGS. 9D and 9E. The proximal and distal deployable wings 912, 914 can be deployed to engage tissue therebetween and to thereby seal the hole in the apical tissue at the implantation site 607 created by the implant 102.

While the distal end 618 of the outer shaft 104 is positioned within the left ventricle 606, a suitable actuator tool that can be received through the outer shaft 104, which can be the same or different from the reversal tool 802, can be used to deploy the distal wings 914 of the closure implant 904, as shown in FIG. 9B. The outer shaft 104 can then be pulled proximally towards the apex 601 of the heart 602 such that it entirely or partially exits the apex 601, as shown in FIG. 9C. This movement of the outer shaft 104 can bring the closure implant 904 in proximity to the apex 601 and the closure implant 904 having the distal wings 914 deployed can be positioned within tissue of the apex 601 as shown by way of example in FIG. 9D. However, it should be appreciated that, in some embodiments, the distal wings 914 can be positioned in the left ventricle 606 outside of the wall of the apex 601 and the middle portion 908 can span the apical wall. Furthermore, in some cases, the distal wings 914 can be deployed after the closure implant 904 is inserted at least partially within the apex 601 in a ready-to-deploy position.

FIG. 9D shows that after the distal wings 914 are deployed, the proximal wings 912 can be deployed to engage tissue between the wings 912, 914. In this way, the puncture in the apical wall created by the implant 102 can be sealed. Following the completion of the deployment of the closure implant 904, the outer shaft 104 can be separated from the closure implant 904 and removed, as shown in FIG. 9E.

The implant in accordance with the described techniques can include a prosthetic valve having any suitable configuration that allows the prosthetic valve to have an unexpanded, or collapsed, configuration for delivery and removal to/from a heart valve and an expanded configuration adopted when the prosthetic valve is deployed within the deficient heart valve.

Depending on its structure, the prosthetic valve can alternatively or additionally be described as configured to be able to move between folded and unfolded configurations. The structure of the prosthetic valve can be selected based on an anatomic environment of a natural valve to be repaired or replaced, patient's characteristics, and/or any other factors.

Figure 10:
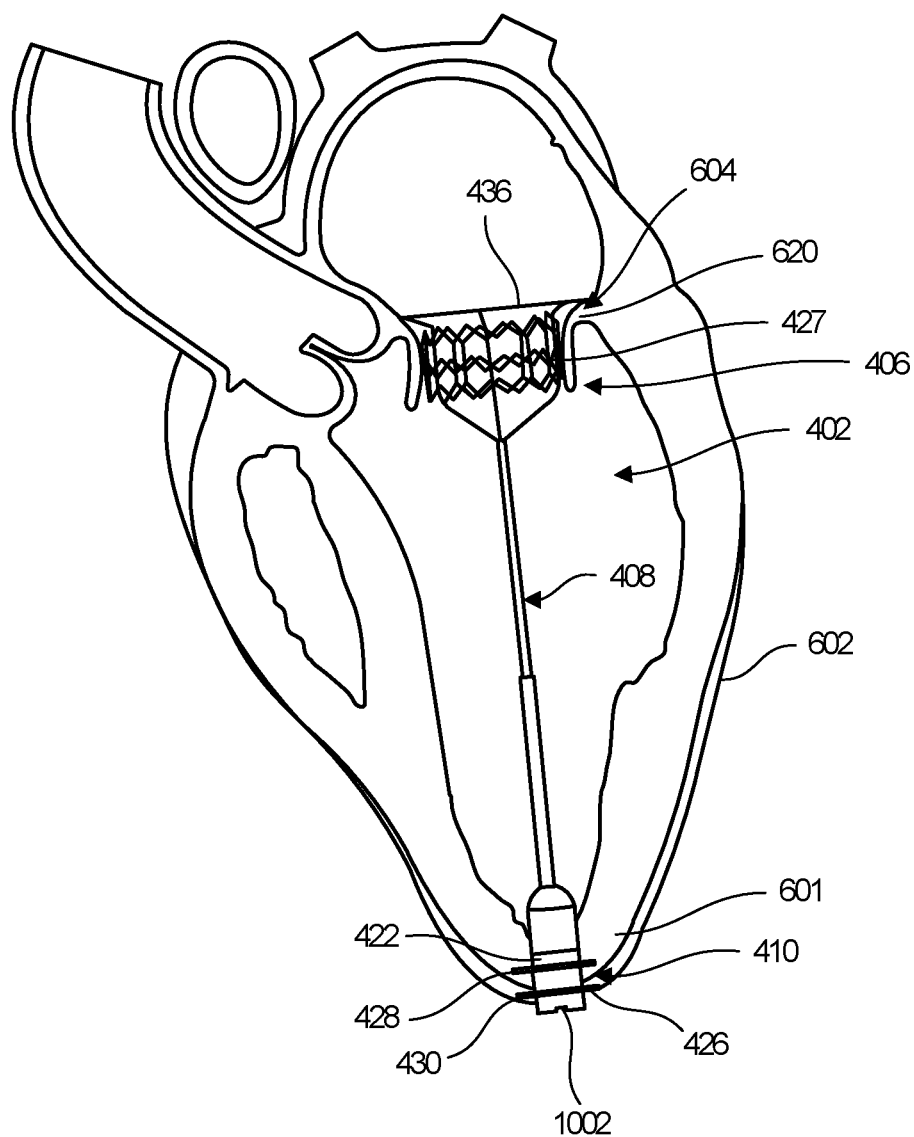
FIG. 10 is a cross-sectional view of the heart with the implant of FIGS. 4A, 4B, 4C, 5A, and 5B deployed in accordance with some embodiments.

FIG. 10 is a cross-sectional view of the heart 602 illustrating the implant 402 of FIGS. 4A-4C, 5A, and 5B transapically delivered to the heart 602 to repair or replace the mitral valve 604. The implant 402 can be deployed within the heart 602 as shown in FIG. 10 removably and replaceably. The implant 402 can have the inner shaft 408 and anchor portion 410 similar to the inner shaft 108 and anchor portion 110 of the implant 102 (shown in a fully deployed configuration in FIG. 6J). However, the implant 402 can also have a prosthetic valve portion 406 configured as an expandable/collapsible wire frame (e.g., a woven wire or other flexible structure). In some embodiments, the prosthetic valve portion 406 can include an insert and lines one or more portions of the valve portion 106 and is configured to provide a seal against the opening of the natural valve or other body opening into which the prosthetic valve portion 406 is inserted. Furthermore, in some embodiments, the expandable/collapsible wire frame can be coupled to the anchor portion 410 by a suture/tether, for example, as shown in FIGS. 5C-5H.

The prosthetic valve portion 406 can be configured to self-expand upon being released from an introducer assembly (e.g., the outer shaft 104, not shown in FIG. 10) used to deliver the implant 402 to the mitral valve 604. As shown in FIG. 10, the prosthetic valve portion 406 can be seated within the opening of the mitral valve 604 such that the positioning member 436, shaped in this example as an expandable/collapsible ring, is configured to engage the tissue of the mitral annulus 620 to suspend the valve body 427 off the tip of the mitral valve 604. The distal and proximal portions 422, 426 of the anchor portion 410 are configured to expand to form deployable wings 428, 430 to anchor the implant 402 to the apex 601, as shown in FIG. 10. In some cases, a proximal end 1002 of the implant 402 can be located in the pericardial space. The proximal end 1002 can be accessed to adjust the distance between the prosthetic valve and the anchor portion affixed to the apex by adjusting a length of the inner shaft 408 or one or more tethers, such as suture tether(s).

After being deployed, the prosthetic valve portion 406 can expand and contract to thereby assist in proper operation of the mitral valve 604. Accordingly, the prosthetic valve portion 406 can be configured to operate so as to eliminate mitral regurgitation during systole. Furthermore, the prosthetic valve portion 406 can operate without impeding the blood flow from the left atrium to the left ventricle during diastole. After the implant 402 is deployed, it can be manipulated such that a distance between the prosthetic valve portion 406 and the anchor portion 410 is adjusted and/or the implant 402 or a portion thereof is rotated.

In embodiments in which the implant includes a tether portion extending between the prosthetic valve portion and the anchor portion (e.g., implant 502, 502', or 502" in FIGS. 5C-5H), the distance between the prosthetic valve portion and the anchor portion can be adjusted by adjusting a length of one or more tethers of the tether portion. The adjustment can be performed at any time point following the implantation (e.g., to adjust the position of the implant after it migrates from an appropriate location), and can also be performed during the placement of the implant. In some cases, the adjustment can decrease or eliminate paravalvular leaks and can treat any other conditions that can be caused by an improper positioning of the implant. FIG. 5B illustrates the mating component 444 (e.g., the distal end 446 of the actuator 442 in FIG. 4C) for engaging a suitable adjustment tool used to adjust the deployed implant 402. The implant 402 can be accessed for adjustment percutaneously and the adjustment process can be guided using a suitable non-invasive technique, such as, for example, fluoroscopy.

It should be appreciated that although illustrated embodiments provide techniques for repairing or replacing a mitral valve, the techniques can be adapted for repairing or replacing other heart valves as well, or for treating any other conditions. For example, a tricuspid valve or an aortic valve can be repaired using an implant in accordance with some embodiments. Also, a left atrial appendage may be repaired using an implant in accordance with some embodiments. As another example, an enlarged ventricle may be reduced in volume using an implant in accordance with some embodiments, and/or a flail valve leaflet may be repaired using an implant in accordance with some embodiments.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of repairing a mitral valve, comprising:
    advancing an outer shaft of an introducer assembly through an apex of a heart into an atrium of the heart;
    deploying a prosthetic valve portion of an implant from the outer shaft in the atrium to cause the prosthetic valve portion to move from an unexpanded configuration to an expanded configuration such that at least a portion of the prosthetic valve portion is disposed within an opening of a mitral valve;
    retracting the outer shaft from the atrium towards the apex of the heart to expose at least one tether coupled to the implant;
    applying tension to the at least one tether; and
    removably affixing an anchor having proximal and distal ends to the heart such that the distal end of the anchor is closer to the opening of the mitral valve than the proximal end, wherein a portion of the at least one tether extends through the anchor and beyond the proximal end thereof; and
    placing an actuator over the portion of the at least one tether to releasably engage the anchor and actuate a lock to reversibly lock the anchor along the at least one tether such that the at least one tether maintains a distance between the prosthetic valve portion and the anchor.

2. The method of claim 1, wherein applying tension to the at least one tether comprises adjusting the distance between the prosthetic valve portion and the anchor subsequent to deployment of the prosthetic valve portion.

3. The method of claim 1, wherein the tether is flexible such that the distance changes as the prosthetic valve portion moves during contraction and relaxation of the heart.

4. The method of claim 1, wherein the lock is accessed percutaneously.

5. The method of claim 1, further comprising, after actuation of the lock to reversibly lock the anchor, releasing the lock and adjusting the at least one tether relative to the anchor to adjust the distance between the prosthetic valve portion and the anchor.

6. The method of claim 1, wherein deploying the prosthetic valve portion causes at least one positioning member on the prosthetic valve portion to be disposed around the opening of the mitral valve to suspend the prosthetic valve portion within the opening.

7. The method of claim 1, wherein the prosthetic valve portion includes an expandable frame, and wherein at least one positioning member on the prosthetic valve portion comprises an expandable ring circumferentially disposed at an end of the expandable frame.

8. The method of claim 1, further comprising determining a position of the prosthetic valve portion using at least one radiopaque marker associated with the prosthetic valve portion.

9. The method of claim 1, wherein removably affixing the anchor to the heart comprises deploying proximal and distal deployable wings on the anchor portion such that the distal wings are deployed against a wall of the apex.

10. A method of repairing a heart valve, comprising:
    delivering an outer shaft of an introducer assembly through an apex of a heart to position a distal end of the outer shaft within an atrium of the heart;
    deploying a prosthetic valve from the distal end of the outer shaft such that the prosthetic valve moves from an unexpanded configuration to an expanded configuration, at least a portion of the prosthetic valve being disposed within an opening of a heart valve;
    retracting the outer shaft from the atrium towards the apex of the heart to thereby expose at least one tether coupled to the prosthetic valve and extending through the outer shaft;
    deploying an anchor having proximal and distal ends at least partially within the apex of the heart such that the distal end of the anchor is closer to the opening of the heart valve than the proximal end, wherein a portion of the at least one tether extends through the anchor and beyond the proximal end thereof; and
    sliding an actuator along the portion of the at least one tether to thereby releasably engage with the anchor and reversibly lock the anchor relative to the at least one tether to maintain a distance between the prosthetic valve and the anchor.

11. The method of claim 10, further comprising, prior to reversibly locking the anchor, applying tension to the at least one tether to adjust the distance between the prosthetic valve and the anchor.

12. The method of claim 10, wherein the tether is flexible such that the distance changes as the prosthetic valve moves during contraction and relaxation of the heart.

13. The method of claim 10, wherein deploying the anchor comprises removably affixing the anchor to the heart by deploying proximal and distal deployable wings such that the distal wings are deployed against a wall of the apex.

14. The method of claim 10, wherein deploying the prosthetic valve causes at least one positioning member on the prosthetic valve to be disposed around the opening of the heart valve to suspend the prosthetic valve within the opening.

15. The method of claim 10, wherein the heart valve comprises a mitral valve.

16. The method of claim 10, wherein the prosthetic valve includes an expandable frame, and wherein at least one positioning member on the prosthetic valve comprises an expandable ring circumferentially disposed at an end of the expandable frame.

17. The method of claim 10, further comprising determining a position of the prosthetic valve using at least one radiopaque marker associated with the prosthetic valve.

18. The method of claim 1, wherein, when the anchor is releasably affixed to the heart, at least a portion of the proximal end of the anchor is positioned in a pericardial space.

19. The method of claim 10, wherein, when the anchor is deployed at least partially within the apex of the heart, at least a portion of the proximal end of the anchor is positioned in a pericardial space.

\* \* \* \* \*